United States Patent
Lampotang et al.

(10) Patent No.: US 12,029,861 B2
(45) Date of Patent: *Jul. 9, 2024

(54) CONTEXT-SENSITIVE FLOW INTERRUPTER AND DRAINAGE OUTFLOW OPTIMIZATION SYSTEM

(71) Applicant: University of Florida Research Foundation, Incorporated, Gainesville, FL (US)

(72) Inventors: Samsun Lampotang, Gainesville, FL (US); Nikolaus Gravenstein, Gainesville, FL (US); Wilhelm K. Schwab, Gainesville, FL (US); David E. Lizdas, Gainesville, FL (US); Francesca K. Enneking, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 921 days.

This patent is subject to a terminal disclaimer.

(21) Appl. No.: 16/890,703

(22) Filed: Jun. 2, 2020

(65) Prior Publication Data

US 2020/0297967 A1    Sep. 24, 2020

Related U.S. Application Data

(63) Continuation of application No. 15/718,235, filed on Sep. 28, 2017, now Pat. No. 10,722,679, which is a
(Continued)

(51) Int. Cl.
*A61M 5/00* (2006.01)
*A61M 1/00* (2006.01)
(Continued)

(52) U.S. Cl.
CPC .......... *A61M 25/0017* (2013.01); *A61M 1/70* (2021.05); *A61M 39/08* (2013.01); *A61M 39/28* (2013.01); *A61M 39/284* (2013.01)

(58) Field of Classification Search
CPC ........ A61M 5/00; A61M 25/00; A61M 31/00; A61M 25/16; A61M 39/02; A61M 27/00;
(Continued)

(56) References Cited

U.S. PATENT DOCUMENTS 3,730,209 A    5/1973  Binard et al.
3,851,650 A    12/1974 Darling
(Continued)

FOREIGN PATENT DOCUMENTS

WO    WO-2012/122267 A1    9/2012

OTHER PUBLICATIONS

U.S. Appl. No. 15/718,235, filed Sep. 28, 2017, U.S. Pat. No. 10,722,679, Issued.
(Continued)

*Primary Examiner* — Leslie A Lopez
*Assistant Examiner* — Ilya Y Treyger
(74) *Attorney, Agent, or Firm* — ALSTON & BIRD LLP

(57) ABSTRACT

Embodiments of the invention provide methods and devices for improved drainage systems and tubing. In one embodiment, a context-sensitive flow interrupter is provided that inhibits or facilitates flow of fluid when engaged with a mating holder. In another embodiment, outflow is optimized through control of the pressure in gas pockets in a tube, drainage tube or assembly. In one such embodiment, gas pockets are vented to inhibit excessive back-pressure or suction on an organ, vessel or cavity being drained. In another such embodiment, loops in the tubes are avoided by using a mechanical template in the form of a groove or peg assembly to thread the slack in the drainage tube to generate
(Continued)

a monotonic gradient. In another embodiment, such as for active drainage systems, a bypass channel is provided that allows an applied vacuum to go around an obstruction created by the collection of fluid in an undrained dependent loop.

15 Claims, 14 Drawing Sheets

Related U.S. Application Data continuation of application No. 13/821,611, filed as application No. PCT/US2011/050810 on Sep. 8, 2011, now Pat. No. 9,962,516.

(60) Provisional application No. 61/381,266, filed on Sep. 9, 2010.

(51) Int. Cl.
  *A61M 25/00* (2006.01)
  *A61M 39/08* (2006.01)
  *A61M 39/28* (2006.01)
  A61M 25/16 (2006.01)
  A61M 27/00 (2006.01)
  A61M 31/00 (2006.01)
  A61M 39/02 (2006.01)

(58) Field of Classification Search
  CPC .... A61M 25/0017; A61M 1/70; A61M 39/28; A61M 39/284; A61K 9/02
  See application file for complete search history.

(56) References Cited

U.S. PATENT DOCUMENTS

| | | | |
|---|---|---|---|
| 4,211,224 A * | 7/1980 | Kubach | A61F 5/441 |
| | | | 604/333 |
| 4,328,828 A | 5/1982 | Cianci | |
| 4,689,047 A * | 8/1987 | Bauer | A61M 25/0606 |
| | | | 604/122 |
| 5,207,661 A | 5/1993 | Repschlager | |
| 5,254,083 A | 10/1993 | Gentelia et al. | |
| 5,356,386 A | 10/1994 | Goldberg et al. | |
| 5,434,418 A | 7/1995 | Schick | |
| 5,582,654 A | 12/1996 | Mansfeld et al. | |
| 5,738,656 A * | 4/1998 | Wagner | A61M 1/85 |
| | | | 604/28 |
| 6,434,418 B1 | 8/2002 | Neal et al. | |
| 6,582,654 B1 | 6/2003 | Kral et al. | |
| 7,524,315 B2 | 4/2009 | Blatt et al. | |
| 7,655,565 B2 | 2/2010 | Manens et al. | |
| 7,883,494 B2 | 2/2011 | Martin | |
| 7,931,630 B2 | 4/2011 | Nishtala et al. | |
| 7,938,817 B2 | 5/2011 | Gelfand et al. | |
| 7,976,533 B2 | 7/2011 | Larsson | |
| 8,403,884 B2 | 3/2013 | Nishtala | |
| 8,486,051 B2 | 7/2013 | Larsson | |
| 8,491,550 B2 | 7/2013 | Ramella et al. | |
| 8,568,387 B2 | 10/2013 | Paz | |
| 8,801,684 B2 | 8/2014 | Walti et al. | |
| 9,216,242 B2 | 12/2015 | Nishtala et al. | |
| 9,622,670 B2 | 4/2017 | Burnett et al. | |
| 9,655,555 B2 | 5/2017 | Burnett et al. | |
| 10,722,679 B2 * | 7/2020 | Lampotang | A61M 25/0017 |
| 2005/0005943 A1 | 1/2005 | Lanier | |
| 2006/0271019 A1 | 11/2006 | Stoller et al. | |
| 2007/0010798 A1 | 1/2007 | Stoller et al. | |
| 2007/0239121 A1 | 10/2007 | Tully et al. | |
| 2008/0191370 A1 | 8/2008 | Pankhurst et al. | |
| 2008/0312550 A1 | 12/2008 | Nishtala et al. | |
| 2009/0221933 A1 * | 9/2009 | Nishtala | A61B 5/205 |
| | | | 600/561 |
| 2010/0130949 A1 | 5/2010 | Garcia | |
| 2010/0137743 A1 | 6/2010 | Nishtala et al. | |
| 2013/0066166 A1 | 3/2013 | Burnett et al. | |
| 2013/0218106 A1 | 8/2013 | Coston et al. | |
| 2014/0074071 A1 | 3/2014 | Paz | |
| 2014/0194835 A1 | 7/2014 | Ehlert | |
| 2015/0095050 A1 | 4/2015 | Murrish et al. | |
| 2016/0183819 A1 | 6/2016 | Burnett et al. | |
| 2016/0244871 A1 | 8/2016 | Mulders et al. | |
| 2016/0310711 A1 | 10/2016 | Luxon et al. | |
| 2017/0020724 A1 | 1/2017 | Burnett et al. | |
| 2017/0136209 A1 | 5/2017 | Burnett et al. | |
| 2017/0138027 A1 | 5/2017 | Chuang | |
| 2017/0156611 A1 | 6/2017 | Burnett et al. | |

OTHER PUBLICATIONS

U.S. Appl. No. 13/821,611, filed Mar. 8, 2013, U.S. Pat. No. 9,962,516, Issued.
PCT/US2011/050810, Sep. 8, 2011, WO 2012/033906, Expired.
U.S. Appl. No. 61/381,266, filed Sep. 9, 2010, Expired.
Tully, S., "Top Vent Study: Optimizing Urine Collection System Flow to Improve Patient Outcomes," Tyco Healthcare Group, Mansfield, MA, May 2007, pp. 1-8.

* cited by examiner

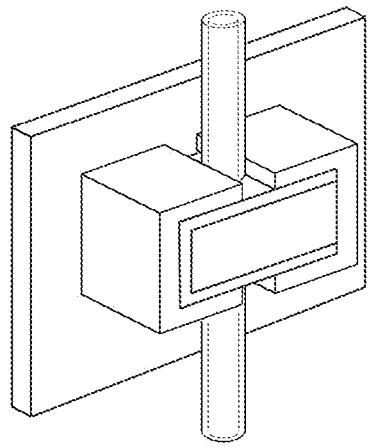 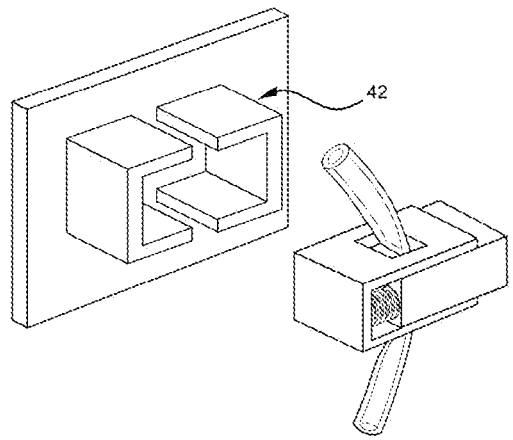
FIG. 4A               FIG. 4B
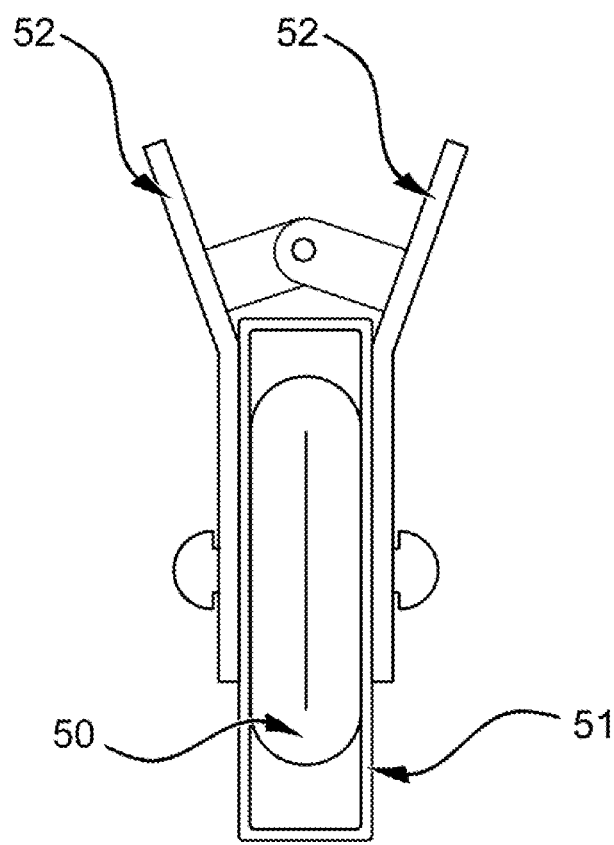 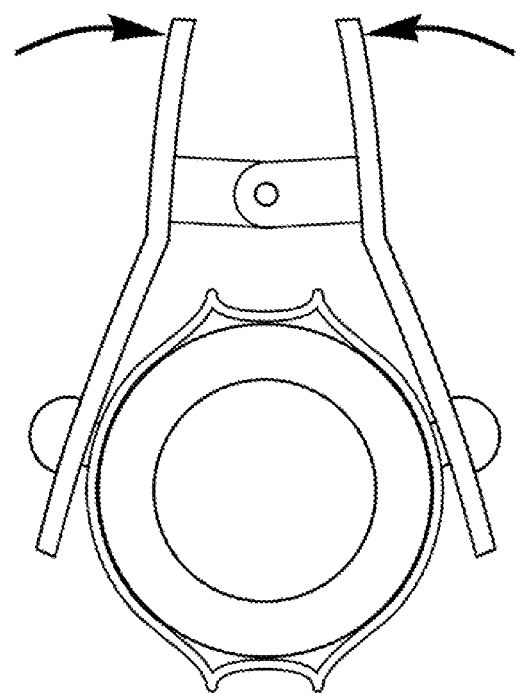
FIG. 5A               FIG. 5B

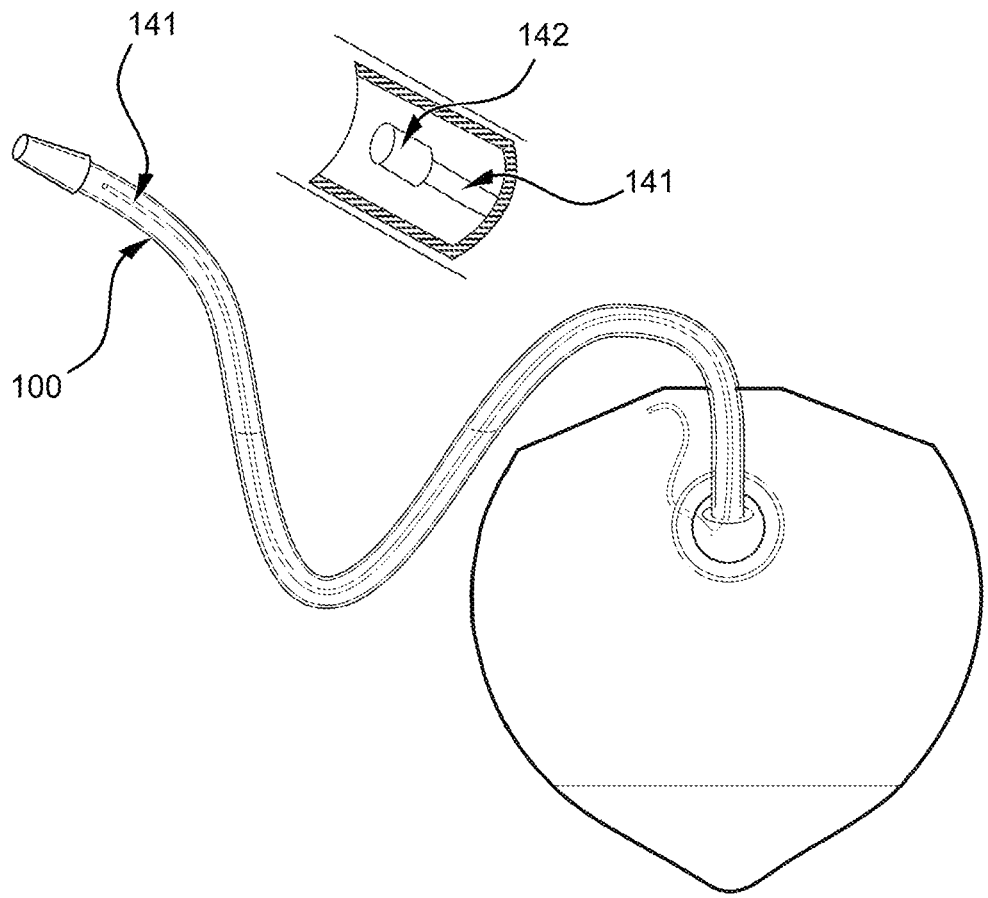
FIG. 14
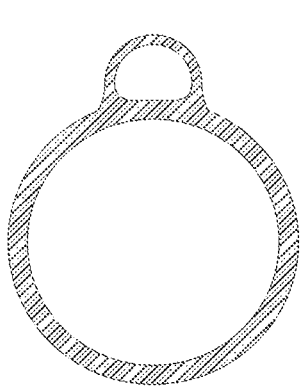 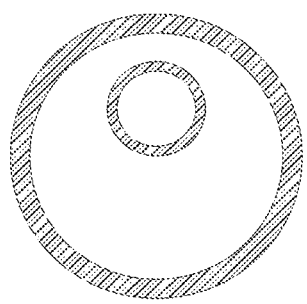 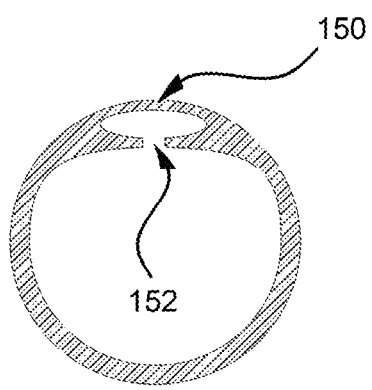
FIG. 15A  FIG. 15B  FIG.15C

CONTEXT-SENSITIVE FLOW INTERRUPTER AND DRAINAGE OUTFLOW OPTIMIZATION SYSTEM

CROSS-REFERENCE TO RELATED APPLICATIONS

This application is a continuation application of U.S. application Ser. No. 15/718,235, filed Sep. 28, 2017, which is a continuation of U.S. application Ser. No. 13/821,611, filed Mar. 8, 2013, which is a national stage application of International Application No. PCT/US2011/050810, filed Sep. 8, 2011, which claims the benefit of U.S. Provisional Application No. 61/381,266, filed Sep. 9, 2010, the disclosures of each of which are hereby incorporated by reference in their entirety, including all descriptions, figures, tables and drawings.

BACKGROUND OF THE INVENTION

Current medical practice requires some body cavities, organs (e.g., the bladder or kidney), spaces (e.g., the pleural space), or wounds of patients to be drained of fluid whether in the liquid form (e.g., urine or blood) or gaseous form (e.g., air, gas) or a gas/liquid mixture (e.g., frothy exudate). For example, current medical practice includes draining blood in a hemothorax and air, gas, or frothy exudate from a pneumothorax.

Examples of urine drainage include urinary catheters inserted via the urethra, nephrostomy tubes, and suprapubic catheters. Nephrostomy tubes are inserted directly in the calyx of the kidney through the patient's back to drain urine from the kidneys. A suprapubic catheter drains urine out of the bladder but is inserted directly into the bladder through the abdominal wall, instead of through the urethra.

Examples of chest and thoracic drainage include pleural drains that are inserted in the pleural space and drain air, gas, or blood or a mixture of both from the pleural space via a chest tube and a chest drainage system, such as the Pleurevac.

Examples of blood drainage include chest tubes for evacuating blood from a hemothorax, wound drainage catheters, and surgical drainage collectors.

An example of mediastinal drainage includes a pericardial catheter that drains blood from the pericardium, the sac surrounding the heart.

Examples of gastrointestinal drainage include nasogastric catheters and drainage tubing that empties into a collection vessel.

It is also widely accepted that to control infection, fluid that has drained from a patient should not be allowed to flow back to the patient.

Also, a drainage system can be active or passive. A passive system can be gravity-operated such as a urine drainage system. An example of an active drainage system is a chest drainage system where a vacuum is applied to the drainage system.

As one particular example, urinary catheters are commonly used for patients who are undergoing surgery, incapacitated due to a spinal injury or pelvic fracture, incontinent with open sacral or perineal wounds, or incapable of voluntary urination in order to permit the drainage of urine. A urinary catheter, such as a Foley catheter, is a flexible, sterile tube that is inserted into the bladder via the urethra to allow the urine to drain into a collection receptacle. Foley bags are a common drainage collection receptacle used to collect urine from a Foley catheter inserted in the urethra. Urine is transferred to the collection bag via a drainage tube connected to the catheter.

A primary risk with urinary catheters is their contribution to urinary tract infections. A urinary tract infection (UTI) is considered a "never" event for which a hospital is not reimbursed by Medicare for treatment costs and also cannot charge the expenses to patients. Therefore, there are incentives for hospitals to follow best practices in order to avoid or reduce catheter associated UTI occurrences in their patients. Accordingly, as one guideline, the Center for Disease Control (CDC) recommends, at page 13 of the 2009 Guidelines for Prevention of Catheter-Associated Urinary Tract Infections, to "keep the collecting bag below the level of the bladder at all times" (Category 1B). This guideline is to prevent backflow of urine to the bladder from the collection receptacle by gravity.

To meet this recommendation, the drainage collection bag is usually hooked onto a support (such as a rail or hospital bed) at a location below the level of the bladder. Most collection bags are also vented, so that the intraluminal pressure of the receptacle and empty drainage tubing is at atmospheric pressure, which facilitates gravity dependent drainage.

It is important for the collecting bag to be hooked below the level of a patient's bladder to help keep the flow of urine downhill towards the collection bag. However, when transporting a patient, the drainage collection bag is often placed on the patient's abdomen or on the transport gurney instead of at the proper lower hanging location. This is usually performed to avoid rips and urine spills due to the collection bag protruding from the gurney when at its proper hanging location.

A problem with placing the collection bag on the belly of the patient is that when the bag is higher than the bladder, it is possible for urine in the bag or tubing to flow back to the patient. This backflow of urine can cause infection and patient discomfort.

Although backflow is a recognized problem, on any drain bag or urine meter bag available on the market, if the bag is squeezed, held upside-down, or held above the level of the patient's bladder, it will not stop 100% of urine from going backwards. Unfortunately, one way-valves (non-return or non-reflux valves) cannot be used to prevent back-flow of urine because the CDC Guidelines for Prevention of Catheter-Associated Urinary Tract Infections (1981 and 2009) state that an unobstructed flow of urine should be maintained.

The unobstructed flow of urine is important because when patients are catheterized, many are passing blood and clots in their urine. In some cases, stones and sediment are passed by the patient. Further, there is often viscous low output urine. If an anti-reflux mechanism or valve is in place, the danger is greater of impeding the free flow of urine and creating a clogging effect at the anti-reflux mechanism. The clogging effect may cause a standing column of urine that may back right up into the patient.

Recent anti-reflux chambers are designed to be an elevated dome chamber above the bag with a right angle then leading into the drainage tubing, which minimizes urine from going back to the patient through the drainage tubing. However, in certain orientations such as the reflux chamber being on the dependent side, the anti-reflux chamber fails and urine is still able to flow retrograde through the anti-reflux chamber and re-enter the drainage tubing.

Another problem with current urinary catheter and drainage bag systems is that when the collection bag is hooked onto the support, the drainage tube between the catheter and the collection bag contains excess slack. As shown in FIG. 1A, this excess slack in the drainage tube 13 between the catheter 14 and the collection bag 10 hooked onto the support 12 (via hook 11) creates a loop (see encircled section), that serves as a basin into which fluid will pool. The term loop in this application will mean any loop, U-loop, and inflection point in a drainage assembly where liquid can accumulate and/or obstruct a cross-section of the tubing.

When the fluid level within the loop rises to fill the tubing's cross-sectional area (see line at trough of FIG. 1B), two separate airspaces are formed (airspace U and D) and air pressure between the two airspaces can no longer equilibrate across the fluid-filled Loop. The air pocket upstream of the loop (airspace U of FIG. 1B) is effectively trapped because it cannot escape back toward the patient or downstream to the drainage bag 10. As more urine flows out, the upstream meniscus U rises and compresses airspace U. Because the trapped amount of air in airspace U is being squeezed into a smaller volume by the rising meniscus U, the pressure in airspace U rises and resists the rise of meniscus U. Thus, as more urine collects in the urine-filled loop, meniscus U barely moves up while meniscus D, which is exposed to atmospheric pressure via the vented collection bag, rises. The rise in pressure in airspace U generates a backpressure that is transmitted back to the bladder 20.

Because the bladder is highly compliant, the bladder responds to backpressure by stretching and accommodating greater undrained urine volumes, while maintaining low intravesical (bladder) pressure. Fluid will accumulate within the bladder until intravesical pressure exceeds the backpressure caused by the air-lock obstruction of airspace U. The pressure at airspace U equals the difference in elevation H between menisci U and D. The maximum difference in menisci elevation across the loop effectively sets the pressure and bladder volume thresholds before urine can crest over the downstream (distal) apex and flow into the collection bag. In-vitro tests have shown that back-pressures of 20 cm $H_2O$ can exist due to a urine-filled loop. The relationship between bladder pressure and volume of urine in the bladder can be understood by reference to the cystometrogram of FIG. 2. As can be seen by the basal cystometrogram, a 20 cm $H_2O$ backpressure on the bladder means that about 425 ml of urine is trapped in the bladder. This high volume of undrained urine is likely a risk factor for urinary tract infections.

Accordingly, there continues to be a need in the art for improved devices and procedures for minimizing the instances of infections and/or reduce backflow or backpressure contribution to those instances of infections.

Although this background describes certain specific applications and problems, embodiments of the invention should not be construed as limited to or requiring the solving of all of these problems.

BRIEF SUMMARY

Embodiments of the invention provide methods and devices for improved drainage systems. As described herein, methods and devices are provided that can aid in controlling pressure within drainage systems. Certain embodiments of the invention can be applied to medical situations in order to address problems with drainage and the resulting pressures felt by internal organs, such as the bladder.

Embodiments of the invention work with and can be adapted for both passive and active drainage systems as well as general purpose tubes other than drainage tubes where air locks and pressurized gas pockets can develop that hinder free flow through the tubes.

In accordance with certain embodiments of the invention, a context-sensitive flow interrupter is provided that can be used within and outside healthcare applications to inhibit flow of fluids.

In one embodiment, the context-sensitive flow interrupter is used to address urine backflow occurrences in urinary catheter and drainage systems, and includes a holding device for a collection bag of the urinary catheter and drainage system. According to a specific embodiment of the invention, a holding device for a Foley bag is provided (instead of the hook currently used in practice) that automatically opens a normally closed clamp. The normally closed clamp is installed on the drainage tube connecting the catheter to the bag or at any convenient location within the Foley assembly (catheter, drainage tube, and bag) where it can prevent backflow of urine when the clamp is closed in instances where the drainage bag or drainage tubing is placed above the bladder. The clamp closes the tube or urine flow passage whenever the clamp assembly is not inserted into its receptacle that is mounted on an operating room (OR) bed, a transport stretcher or gurney, a wheelchair, a procedure table, etc. When the clamp assembly is inserted into its receptacle to "hang" the Foley bag, the clamp is automatically opened providing unobstructed flow to urine, blood, stones and sediments. It is also contemplated that other flow interrupters such as stopcocks, ball valves, and cuffs can be used instead of a clamp.

Presently, a caregiver must hang the Foley bag at a location below the bladder of a patient. In addition, when transporting the patient, a caregiver often unhooks the Foley bag and moves the bag from its hanging position. Therefore, with certain embodiments of the invention, no extra steps are required to operate the flow interrupter. Rather, the process of "hanging" the bag automatically opens the clamp or stopcock of the flow interrupter. Similarly, the process of "unhooking" the bag from its holder closes the clamp or stopcock, thereby inhibiting urine from back-flowing from the Foley bag. Advantageously, no new motions are required to be performed and the caregiver does not need to remember to do anything other than what the caregiver is used to performing. In certain embodiments, the process of milking the drainage tube can also activate a context-sensitive flow interrupter which could be placed at the proximal end of the drainage tube or at the site where loops are most likely to form. In an embodiment, a context-sensitive flow interrupter can be incorporated at or near the drainage bag.

The clamp or stopcock can be made of any suitable material. For example, the clamp can be made of spring steel or resilient plastics. The stopcock can be a ball valve.

The holder for the flow interrupter and bag can be mounted on the OR bed or stretcher or transport gurney or wheelchair such that it holds the Foley bag in a way that the bag does not protrude from the bed/stretcher/gurney/wheelchair. In a further embodiment, the bag holder/flow interrupter opener can be mounted on a lockable swing arm that would allow the option to swing the Foley bag out so that the Foley bag protrudes from the OR bed in a manner allowing an anesthesia provider to read the volume of contents in the Foley bag via its graduated markings while standing at the anesthesia machine.

In other applications of the context-sensitive flow interrupter, the flow interrupter could be normally open instead of normally closed.

According to an embodiment where the context-sensitive flow interrupter uses a stopcock, the state (closed or open) of the stopcock is toggled when inserting into or removing from a holder.

According to certain embodiments of the invention, a drainage outflow optimization system is provided to improve urine outflow and minimize undesired backpressure or suction at the bladder.

In one embodiment, a system is provided that eliminates or substantially reduces formation of loops and inflection points where liquid can collect to inhibit undesired generation of backpressure and/or suction. In another embodiment, a system is provided that minimizes backpressure and/or suction even in the presence of loops where liquid can collect and obstruct the tubing cross-section.

In a specific embodiment example, a mechanical template capable of shaping a tube is provided to achieve a monotonic downward gradient of a drainage tube, reducing formation of loops. The mechanical template can include a zigzag groove, spindle or series of hooks or pegs. Because no modifications to the drainage tube are necessary in order to adopt mechanical templates of embodiments of the invention, the subject mechanical templates to shape a tube work with existing drainage assemblies, such as the standard Foley assemblies that are currently in use. In certain embodiments, the mechanical templates can be provided in kits.

According to one embodiment of the subject mechanical templates to shape a tube, a groove can be provided on a holder. The groove can have a zig-zag or some other pattern on the sloped plane. The Foley tubing can be snapped into the groove ensuring that the Foley tubing has a monotonic negative (downward) gradient that will inhibit the formation of loops where liquid can collect. The groove can also be carved out of a flat slab of material that is attached to an IV pole, OR bed, wheelchair, etc.

For embodiments incorporating the context-sensitive flow-interrupter, the clamp or stopcock or other flow interrupter can be inserted into a receptacle upon running the drainage tube through the mechanical template. A thinner walled drainage tube (as compared to the current Foley tubing) may be used to allow the use of a lower-force clamp to occlude the drainage tubing as compared to that used for a thicker walled drainage tube.

According to another embodiment, backpressure and/or suction is alleviated by a venting or bypass system in the drainage tube. The venting system can provide a pressure adjustment along one or more locations within the drainage tube or Foley assembly, including at the bladder itself. In the case of bladder venting, one or more venting lumen that vent to atmosphere or other desired pressure is built into the wall of the Foley catheter with vent ports at the vent tip or catheter portion inside the bladder. The venting system can include a venting tube or bypass tube within the drainage tube or at least one venting or bypass lumen extruded within a wall of the drainage tube.

When a multitude of venting lumens is used, the vent ports may be situated at different locations within the Foley assembly so that any gas pockets at the corresponding vent ports may be vented. A single lumen extruded along the length of a drainage tube may also have a multitude of vent ports along its length that open to the interior surface of the drainage tube and/or its exterior surface depending on the desired application.

The venting system can vent to atmosphere so that pressure in the vented space equilibrates to atmospheric pressure. It can also vent to a pressure above atmospheric (supra-atmospheric) pressure or below atmospheric (sub-atmospheric). If the Foley catheter is placed below the patient's thigh, instead of above the patient's thigh as is usually the case, there may be concern that the Foley catheter may create a slight undesirable siphon effect on the bladder. To counteract this potential siphon effect, airspace U (see FIG. 1B) may be vented to an adjustable supra-atmospheric pressure. According to certain embodiments of the invention, this supra-atmospheric pressure can be obtained via mechanisms such as a spring-loaded valve that only allows gas to flow when a desired pressure is reached, a ball of specific weight that occludes a flow passage and is lifted when the desired pressure is reached, thus allowing gas to flow, or a gas outlet immersed into water whereby the depth of immersion of the outlet below the water surface determines the backpressure. Vents at the Foley catheter portion inside the bladder (as previously described) that vent to atmosphere can be used to counteract a potential siphon effect on the bladder.

In a further embodiment, the venting system can incorporate a backpressure adjuster, where gas pockets in the drainage tube are vented to a drainage receptacle vented at atmospheric pressure via a venting tube. The drainage receptacle can contain fluid and may even be the drainage bag. One end of the vent tube can be controllably immersed in fluid in the receptacle in order to adjust the backpressure.

While specific embodiments and features described herein are directed to urine drainage and Foley assemblies, which provide concrete examples of fluid backflow prevention and fluid outflow optimization, the applicability of embodiments of the invention to other drainage applications such as urine, chest, blood and mediastinum drainage and active and passive drainage systems as well as non-drainage tubing in light of the embodiments of the invention described herein should be readily apparent.

It should be understood that although this Summary presents selected concepts and features described in more detail in the Detailed Description, it should be understood that the Summary is not intended to identify key features or essential features of the claimed subject matter or to limit the scope of the claims.

BRIEF DESCRIPTION OF THE DRAWINGS

FIGS. 4A and 4B show representations of a context-sensitive flow interrupter according to another embodiment of the invention.

FIGS. 5A and 5B show representations of a context-sensitive flow interrupter with a spring clamp configuration according to an embodiment of the invention, where FIG. 5A shows the normally-closed position and FIG. 5B shows the open position.

FIGS. 6A and 6C show the normally-closed position and FIGS. 6B and 6D show the respective open position.

FIG. 14 shows a representation of a venting/bypass system with internal venting/bypass tube according to an embodiment of the invention.

FIGS. 15A-15C show representations of a venting/bypass system with extruded venting/bypass lines according to an embodiment of the invention.

DETAILED DISCLOSURE

Figure 1A:
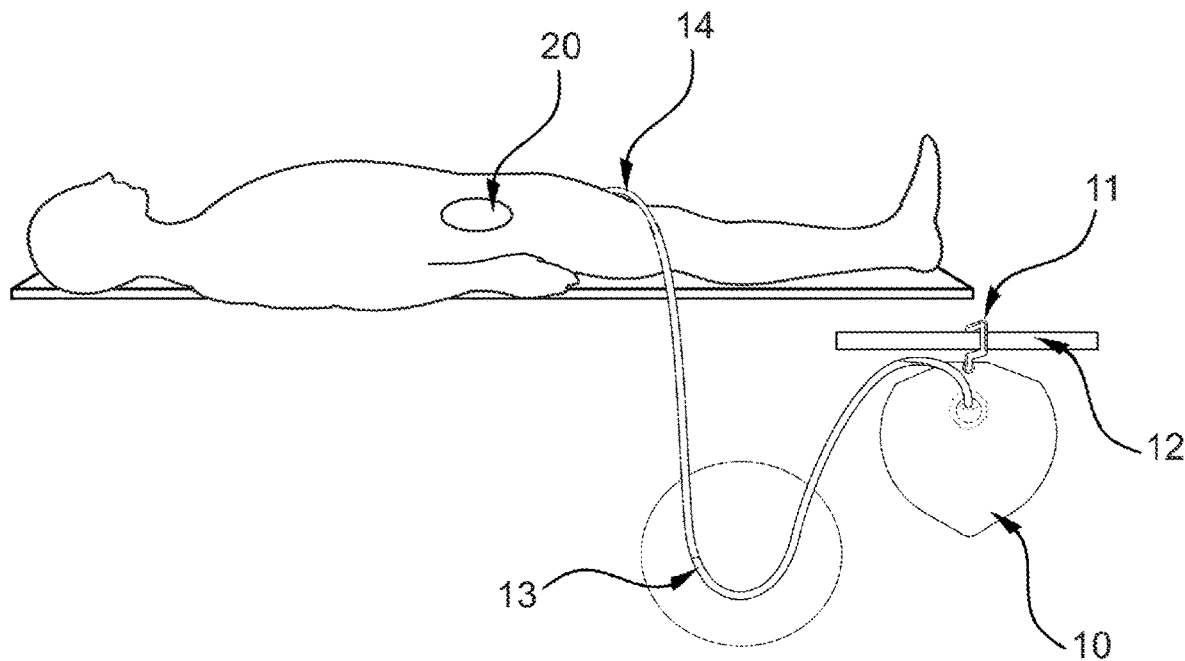
FIGS. 1A and 1B show a typical urinary catheter and drainage bag system and illustration of airspace backpressure formation.

Embodiments of the invention provide methods and devices for improved drainage systems. The subject methods and devices can be used within and outside healthcare applications to contextually inhibit flow of fluids and/or optimize fluid outflow. Within the healthcare applications, the drainage systems can be for body cavities, organs, spaces, or wounds.

Certain embodiments of the invention are directed to minimizing instances of urinary tract infections by effective means of inhibiting urine back-flow from a drainage bag back to the patient and minimizing undesirable back-pressure and/or suction. Although embodiments directed to urinary catheter drainage systems are described in detail herein, the subject devices and methods can be applied to other fluid systems outside of urinary catheter drainage systems, and even outside of medical applications, where optimization of drainage or outflow and context-sensitive control of fluid flow are desired.

In current practice with respect to urinary catheter drainage systems, because Foley bags and connecting tubing are generally hung from the patient's bed, there is almost inevitably a loop of the drainage tubing that hangs below the collection bag and allows liquid to accumulate and create the possibility for a water trap, airlock, and backpressure that is transmitted to the bladder and renal system. Currently, some clinicians will take the time to empty the accumulated urine out of the urine drainage tubing while others may not. The urine is emptied by lifting the drainage tubing so that the accumulated urine can flow by gravity into the collection bag. This process of emptying the drainage tubing is sometimes called "milking". During milking, there is also the possibility of retrograde flow of urine from the drainage tubing back to the bladder if the tubing is raised above the bladder level or a pressure gradient is established that promotes retrograde urine flow.

During and/or after milking there is also the possibility of establishing a sub-ambient pressure (suction), which may cause bladder tissue to wrap around the tip of the Foley catheter and cause trauma. Referring again to FIG. 1B, one visual for determining that suction is occurring (with sub-ambient pressure at airspace U) is when meniscus U in the upstream leg is higher than meniscus D in the downstream leg of the tubing.

In accordance with an embodiment of the invention, a context-sensitive flow interrupter is provided that can inhibit back flow of urine from a drainage bag when the drainage bag is not properly secured or during milking of the drainage tubing, i.e., emptying the drainage tubing of accumulated liquid. Although the subject context-sensitive flow interrupter is described herein for addressing problems with urine back-flow, embodiments of the invention are not limited to such applications. For example the context-sensitive flow interrupter can be implemented for any application where fluid is to be inhibited from returning to its source or flow is to be interrupted at certain times while providing unobstructed flow at other times.

In one embodiment, the context-sensitive flow interrupter has two parts —a holder portion and an actuator portion— that when interacted form a context-sensitive flow interrupter that can inhibit flow of fluid. The actuator portion of the flow interrupter can be a clamp that functions as a normally closed clamp. Therefore, unless the actuator portion is inter-locked with the holder portion, fluid cannot flow between the drainage bag and the drainage tubing. The holder can have a receptacle for the actuator portion of the flow interrupter. When the actuator portion is inserted into the holder, the normally closed function of the actuator portion is released and fluid flow is unobstructed. The drainage tubing can have a section of tubing particularly adapted for the actuator portion of the flow interrupter.

Figure 3A:
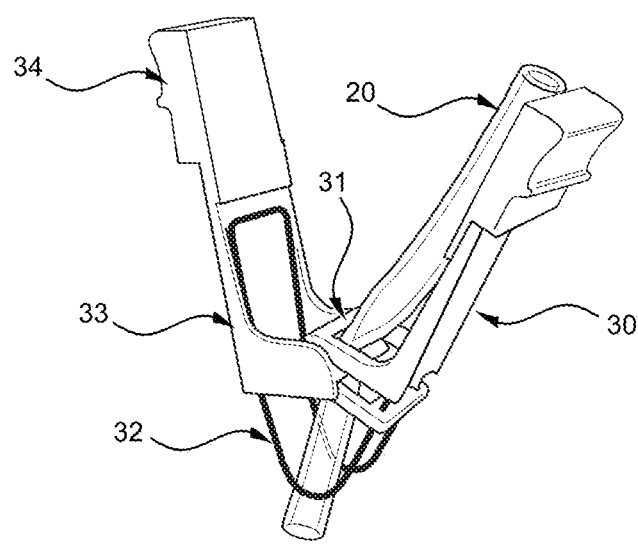
FIGS. 3A, 3B and 3C show representations of a context-sensitive flow interrupter according to an embodiment of the invention.

According to one embodiment, such as shown in FIG. 3A, the section of tubing 20 particularly adapted for the actuator portion of the clamp 30 allows for an external jaw 31 to be affixed that has a spring mechanism 32 keeping the jaw 31 closed and the section of tubing 20 in a clamped position. Arms 33 can extend from the jaw 31, the arms 33 being connected to the spring mechanism 32 such that bringing the arms together causes the spring mechanism to open the jaw 31 and thereby open the section of tubing 20. The arms 33 can include handles 34, which can be ergonomically formed for ease of use. The actuator portion of the clamp 30 can be made of any suitable material. For example, the spring mechanism 32 and the arms 33 and jaw 31 of the actuator portion of the clamp can be made of spring steel or resilient plastics.

Figure 3B:
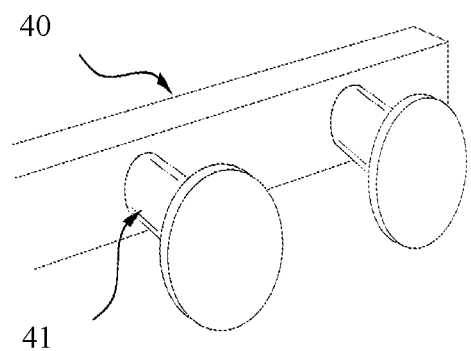
Figure 3C:
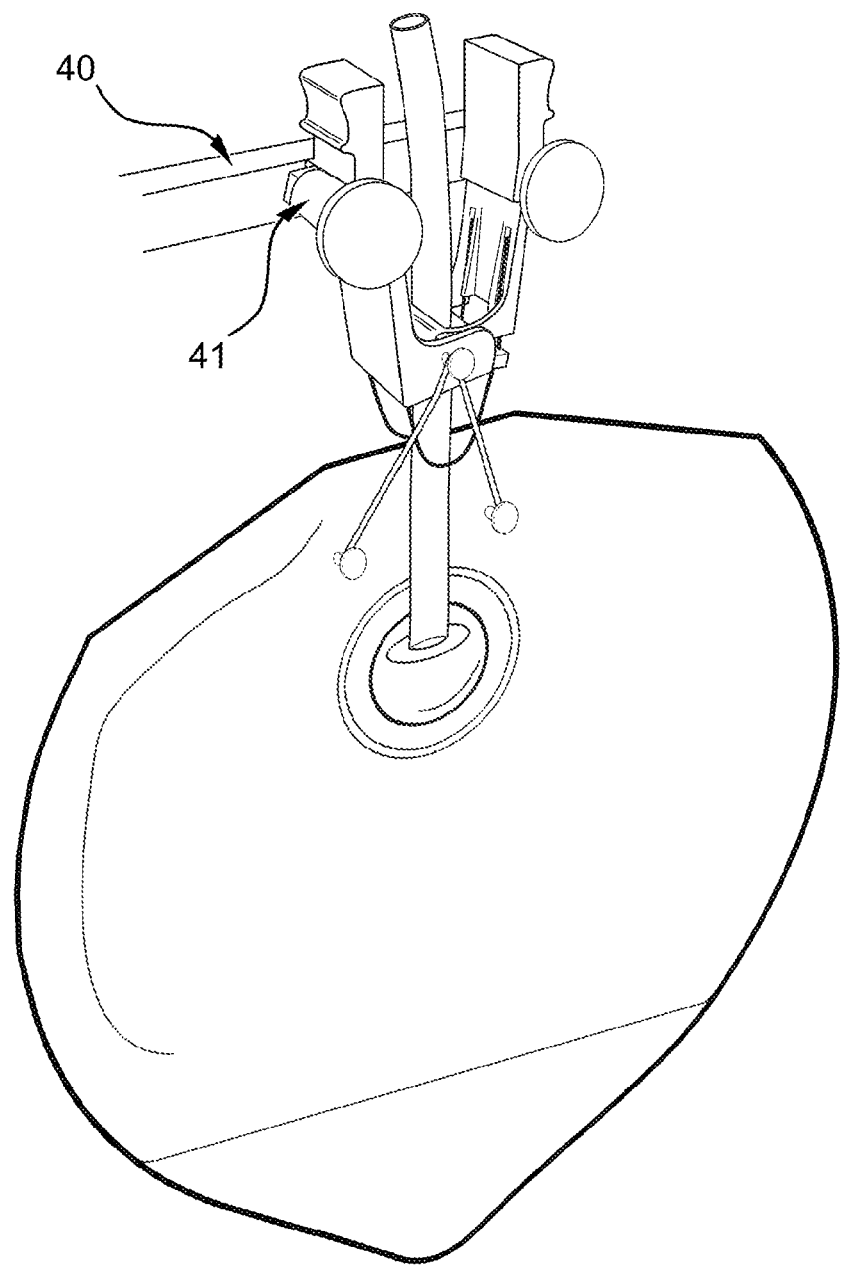

According to one embodiment shown in FIG. 3B, the holder portion of the clamp 30 can have a receptacle in the shape of two rods 41 protruding from the side of the holder portion 40 such that when the actuator portion with clamp 30 is inserted downward, between the two rods 41, the spacing between the two rods 41 cause the handles 34 (or arms 33) of the clamp 30 to come together and thereby opens the clamp 30 (FIG. 3C). In one embodiment, the rods 41 have concentric rollers inserted over them to assist in insertion. The handles 34 (or arms 33) may also have notches (not shown) that positively and securely engage the rods/rollers to create a detent position when the clamp 30 is fully inserted in the holder. For illustration, the bag is shown attached to the clamp by a string that allows the bag to hang from the clamp when the clamp in inserted in its receptacle. This also fixes the location of the tubing relative to the clamp. Other means of attachment of the bag to the clamp are possible including a keyed means that would make it difficult to hang or attach the bag on anything else but a holder having a mate to a key portion associated with the bag.

According to another embodiment, as shown in FIG. 4B, brackets 42 can be used to cause the actuator portion of the clamp 30 to open. The brackets 42 can be disposed so that the actuator portion is inserted perpendicular to a vertical axis (FIG. 4A).

The holder portion receptacle can be mounted on an OR bed, a transport stretcher or gurney, a wheelchair, procedure table, or other apparatus. When the clamp assembly is inserted into its receptacle to "hang" the Foley bag, the clamp is automatically opened providing unobstructed flow to urine, blood, stones and sediments. The holder for the clamp and bag can be mounted on the OR bed or stretcher or transport gurney or wheelchair, such that it holds the Foley bag (or other drainage collection receptacle) in a way that the bag does not protrude from the bed/stretcher/gurney/wheelchair. In a further embodiment, the bag holder/clamp opener can be mounted on a lockable swing arm that would allow the option to swing the Foley bag out so that the Foley bag protrudes from the OR bed in a manner allowing an anesthesia provider to read the Foley bag while standing at the anesthesia machine.

According to another embodiment of the invention, the section of tubing of the actuator portion of the context-sensitive flow interrupter is formed with elastic/deformable yet rigid material on the outer walls of the tubing, within the walls of the tubing, or as a separate section of tubing that wants to remain in a collapsed position (i.e., touching together) until released by the holder.

In one embodiment as shown in FIGS. 5A and 5B, the releasing mechanism can be similar to the jaw opening spring clamp. According to an embodiment, a spring mechanism such as spring form 51 is disposed around a section of tubing 50 to cause the tubing to be in a collapsed position. Two rigid beams 52, or arms, are externally attached to the spring form 51, such that when the tubing portion is inserted into the holder, the two arms 52 come together at their distal ends, forcing their proximal ends to spread open and cause the spring form 51 to spread and the collapsed section of tubing to open as shown in FIG. 5B. The section of tubing that the arms connect to can be flexible and/or deformable, allowing for a clamping effect without causing damage to the tubing.

Figure 6A:
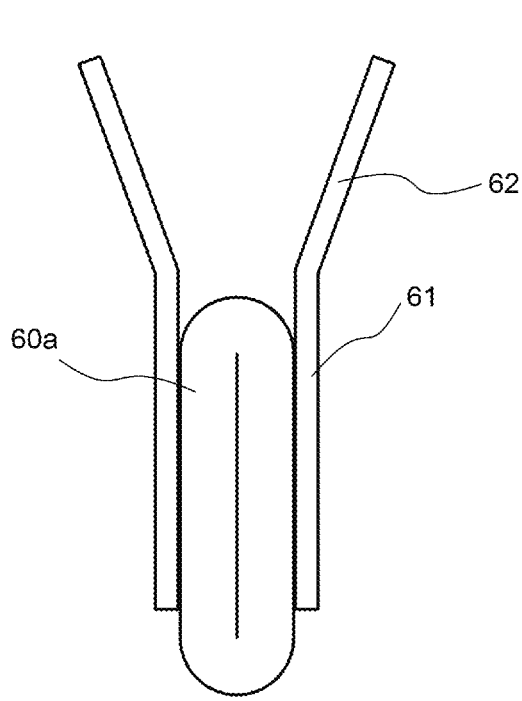
FIGS. 6A-6D show representations of a context-sensitive flow interrupter using a deformable resilient material according to an embodiment of the invention, where
Figure 6B:
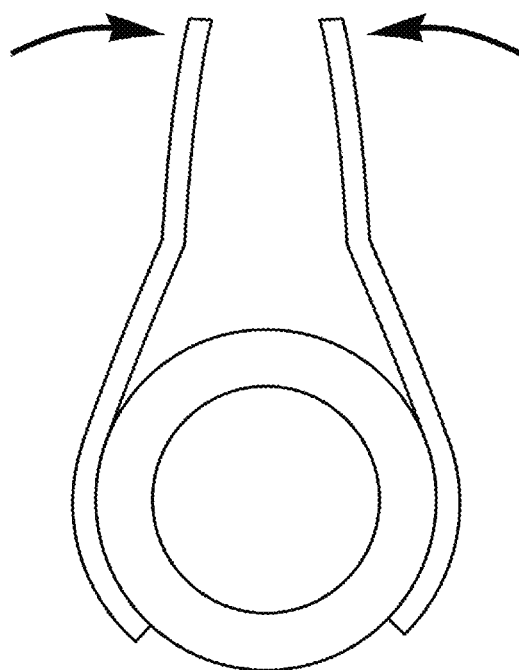
Figure 6C:
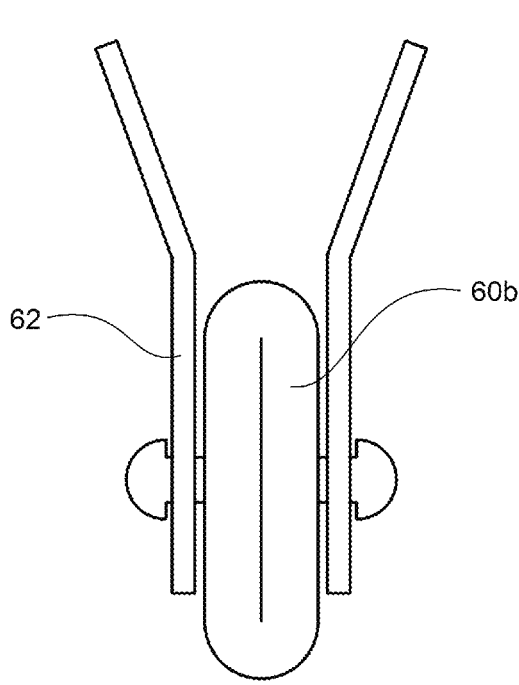
Figure 6D:
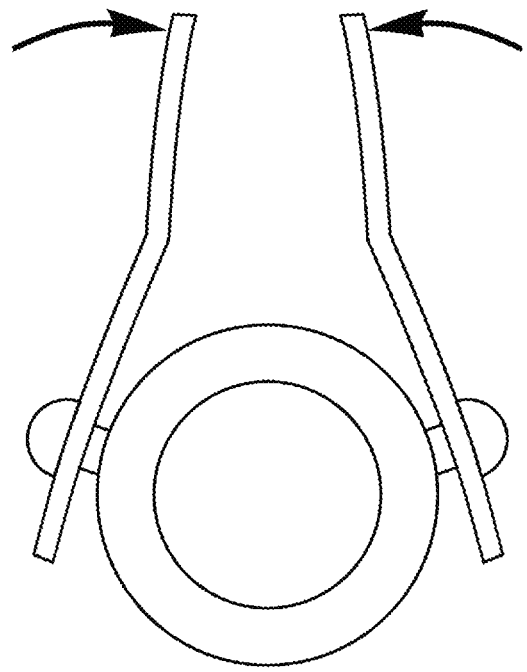

In another embodiment, as shown in FIGS. 6A-6B, resilient material 61 can be disposed at the outer walls of a section of tubing 60a. The resilient material 61 prefers to be in a position that causes the section of tubing 60a to close. When rigid arms 62 attached to, or connected with, the resilient material 61 are pivoted inward, the resilient material moves with the rigid arms and may pop out to allow for a circular cross-section. In yet another embodiment, as shown in FIGS. 6C-6D, the section of tubing 60b having the rigid arms 62 attached can be formed of a resilient material that prefers to be in a collapsed position. Then, the pivoting of the rigid arms 62 causes the section of the tubing 60b to be forced in an open position. The rigid arms can be affixed to the section of the tubing with a portion along the cross-sectional circumference of the section of tubing. The portion of the rigid arm 62 along the cross-sectional circumference of the section of tubing can extend to the extent necessary to keep the section of tubing open and allow unobstructed flow of urine.

Figure 7A:
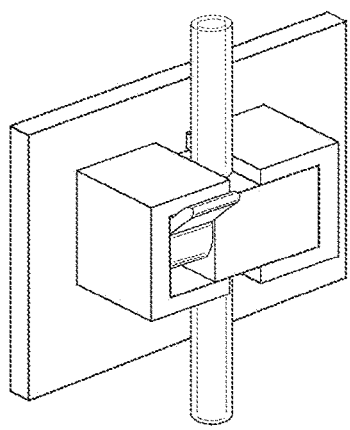
FIGS. 7A and 7B show representations of a context-sensitive flow interrupter using a stopcock according to an embodiment of the invention.
Figure 7B:
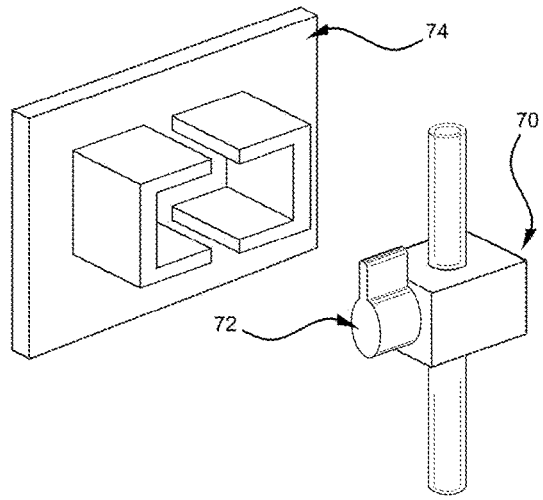

According to another embodiment, the context-sensitive flow interrupter can be in a form of a stopcock. For example, referring to FIG. 7B, a stopcock 70 can be provided in which a turn of its handle or lever 72 opens and closes a path between the drainage tube and a collection bag. In one embodiment, a spring mechanism can be attached to the handle such that the handle causes the stopcock to remain closed (or alternatively to remain open) until the actuator section is received by the holder. By inserting the actuator section into the receptacle on the holder 74, the receptacle can cause the handle to turn and remain in a position whereby the stopcock is open (or closed), such as shown in FIG. 7A.

The section of tubing having the actuator portion of the subject flow interrupter can be disposed at or near the connection of the drainage tube to the drainage bag. The actuator portion can be disposed at or near where the hook is disposed in present Foley bags and replace the hook and string.

According to the CDC guidelines, a caregiver must hang the Foley bag at a location below the bladder of a patient, and therefore currently hooks the Foley bag to the bed or wheelchair of the patient. However, when transporting the patient, a caregiver often unhooks the Foley bag and moves the bag from its hanging position. The subject context-sensitive flow interrupter performs its function as the caregiver hangs and removes the Foley bag from its location at the bed or chair of the patient. Therefore, no extra steps are required to operate the clamp. Rather, the process of "hanging" the bag automatically opens the clamp (or stopcock or other flow interrupter). Similarly, the process of "unhooking" the bag from its holder closes the clamp (or stopcock or other flow interrupter), thereby inhibiting urine from back-flowing from the Foley bag. Advantageously, no new motions are required to be performed and the caregiver does not need to remember to do anything other than what the caregiver is used to performing.

As previously described, the currently used combination of a Foley catheter, drainage tube and collection bag can elevate the pressure in the drainage tube and potentially the patient's bladder, which may in turn inhibit renal function. Specifically, a Foley assembly generally includes a) a Foley catheter inserted into the urethra, b) a drainage receptacle or collection bag (also referred to as a Foley bag) that collects the urine and is vented to atmosphere and c) drainage tubing that channels flow from the Foley catheter to the Foley bag. Foley bags are usually hung under a patient. The excess length of drainage tubing will usually form a loop while in clinical use. Such loops can be referred to as dependent loops. When filled with urine, the loop forms a water trap. In order for liquid to flow from the bladder into the Foley bag in the presence of a urine-filled loop, the urine in the drainage tube must be lifted up and over the downstream leg of the loop.

In accordance with the principles of hydrostatics, the fluid pressure at equilibrium in the Foley catheter distal tip indicates that the bladder pressure is equal to the pressure in the air column (airspace U) of the drainage tube minus the vertical elevation (in units of length of urine) of the Foley catheter's distal tip with respect to the bladder. In practical terms, the pressure in the bladder may be slightly less (only a few cm $H_2O$) than the pressure in the air column. This pressure difference may be dependent on whether the Foley catheter portion external to the patient is routed above or below the patient's thigh.

Figure 1B:
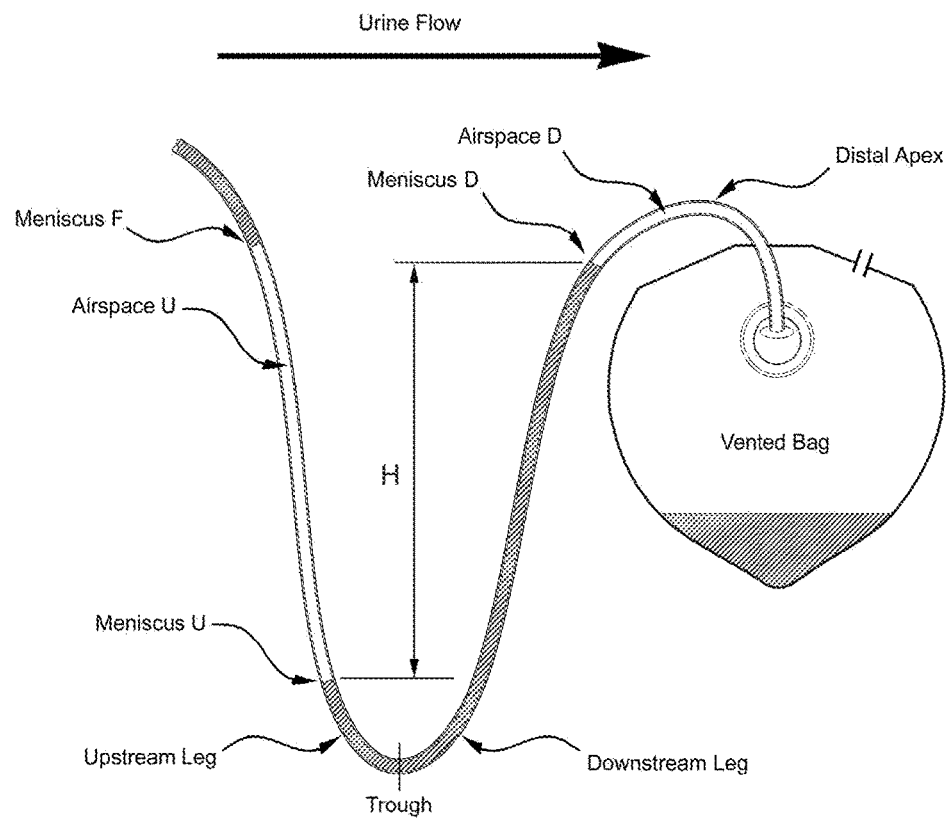

The pressure (or suction) in the compressed airspace U is indicated by the difference H in meniscus elevation between meniscus U and meniscus D as shown in FIG. 1B. In one embodiment of the invention, a device is provided to measure the difference H and thus the backpressure (or suction) on the bladder (and through the cystometrogram, the retained undrained urine volume). In a specific embodiment, the measuring device is in the form of a sheet with a grid of known spacing. In another embodiment, the measuring device is in the form of a perpendicular rod with a graduated movable scale and two adjustable horizontal sliders that are slid to the level of the menisci so that H can be readily measured. In yet another embodiment example, the measuring device is in the form of a laser measuring device that reads the elevation of each meniscus and then calculates H by subtracting the lower elevation from the higher elevation.

In-vitro experimental tests established that the maximum pressure in the air column in the upstream leg of the loop must be high enough to push the column of urine up and over the lip or apex of the downstream leg of the loop. The pressure in the air column in the upstream leg of the loop that forces urine up the downstream leg of the loop and into the drainage bag is experienced as backpressure on the bladder, and may thus, in turn, affect the patient's renal system. In particular, the increased pressure in the air column exerts a backpressure on the bladder and may thus inhibit normal bladder and/or kidney function. Outflow from the bladder is significantly augmented when the drainage tubing is "milked", i.e., cleared of the urine collected in the loop, thus effectively removing the back pressure on the bladder and allowing it to empty.

Referring again to FIG. 1B, the urine collection bag hanging under the patient results in formation of a loop in the drainage tubing and allows for the formation of a liquid trap in the bottom of the loop. As urine enters the tube, gravity causes it to pool in the bottom of the trap; the level quickly rises and blocks the cross-section of the tube. The fluid in the bottom of the trap is bounded by two menisci—an upstream meniscus and a downstream meniscus, respectively. The height of the downstream meniscus is limited by the height of the downstream leg of the loop (the height of the distal apex).

In addition, because the Foley catheter is of sufficiently small internal diameter that it "gets wet and stays wet," with a resulting column of fluid held by the Foley catheter, at the downstream end of this column, there is a meniscus that is referred to herein as the Foley meniscus—meniscus F. Between the Foley meniscus F and the upstream meniscus U there is an airspace U, which can occupy most of the upstream leg of the loop. Newly arriving urine that trickles down the descending leg of the drainage tube (i.e., "open" channel flow) merges with the fluid in the bottom of the trap. The pressure in airspace D (the air pocket above the downstream leg of the loop) is atmospheric pressure because it is in pneumatic connection to the Foley bag that is vented to atmosphere. As incoming urine is added to the loop, the urine will try to distribute equally between the two legs of the loop. However, as meniscus U rises through the addition of urine, the fixed mass of air in airspace U is forced to fit into a smaller volume and is thus compressed. As a consequence, the pressure in airspace U rises as more and more urine flows into the loop. The pressure in airspace D remains constant at atmospheric pressure. Thus, the difference in pressures between airspaces U and D drives the meniscus D up the downstream leg as shown in FIG. 1B. The difference in pressures in cm $H_2O$ (or more accurately in cm of urine) between airspaces U and D is the height difference in cm between menisci U and D.

Figure 2:
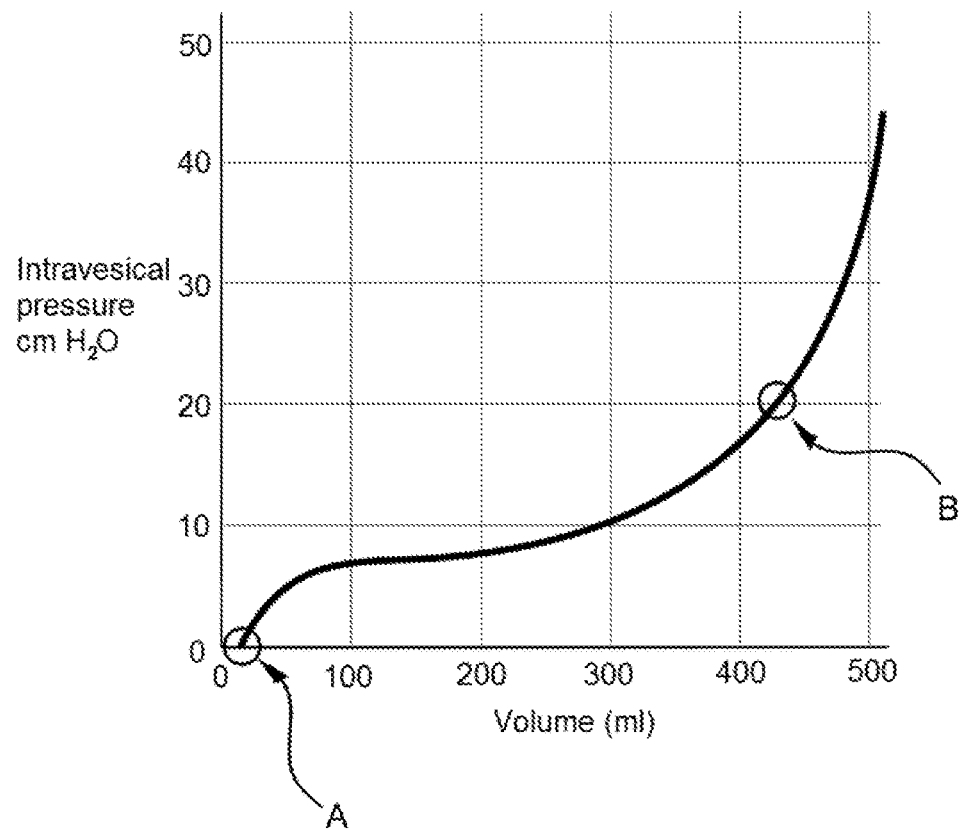
FIG. 2 shows a typical cystometrogram, the compliance curve for the bladder.

As previously mentioned, a urine-filled loop may place as much as 20 cm $H_2O$ backpressure on the bladder, which means that about 425 ml of urine is trapped in the bladder of a typical adult patient (point B). However, clinicians have worked on the assumption, which is flawed, that a patient who has a Foley assembly is at the ~20, 0 coordinate (point A) on the plot of FIG. 2—, i.e., an almost empty bladder. However, due to the back-pressure caused by loops, the catheter does not always drain the bladder completely. Therefore, the current standard drainage tube and drainage collection systems lead to a high incidence of large residual urine volumes due to this loop back pressure phenomenon.

Moreover, the prevalence of dependent loops and undrained dependent loops in clinical environments has been quantified and appears to be a real healthcare issue. In a prevalence study in a tertiary care hospital, 76 of 88 (87%) urine drainage systems in use with patients had a dependent loop. Of the urine drainage systems with dependent loops, 84% had undrained fluid in them with differences in meniscus elevation as high as 26 cm, indicating back pressures as high as 26 cm $H_2O$ being applied to the bladder.

The common clinical practice of lifting the loop, moving or milking the tube, or "walking the fluid" down the tube may or may not solve the problem of backpressure formation. This is because the same condition may develop again, over time, leading to the same backpressure, or a siphon can form that may undesirably transmit negative pressure or suction to the bladder.

Accordingly, certain embodiments of the invention are directed to outflow optimization of drainage systems. By equalizing the pressures in airspaces U and D inside the drainage tube, the bladder can be protected from high backpressure and difficulties in emptying. In one embodiment, backpressure is alleviated in drainage tubes by preventing the formation of loops where liquid can collect through the creation of a monotonic downward gradient. In another embodiment, backpressure is alleviated in drainage tubes by venting the trapped, compressed air in an upstream portion of a drainage tube to atmosphere, supra-atmospheric pressure or sub-atmospheric pressure.

In accordance with certain embodiments of the invention utilizing venting for control of pressure and fluid drainage, the vents are two-directional. That is, gas or air flow is able to travel in two directions—into and out of the drainage tube. The two-way directionality can be achieved by using gas-permeable membranes. The bi-directionality of flow allows pressure within the drainage tube to be relieved by allowing gas to flow out of the drainage tube but, contrary to a unidirectional valve, also allows gas to flow into the drainage tube, for example, air from the atmosphere to relieve unwanted suction or sub-ambient pressure.

Figure 8A:
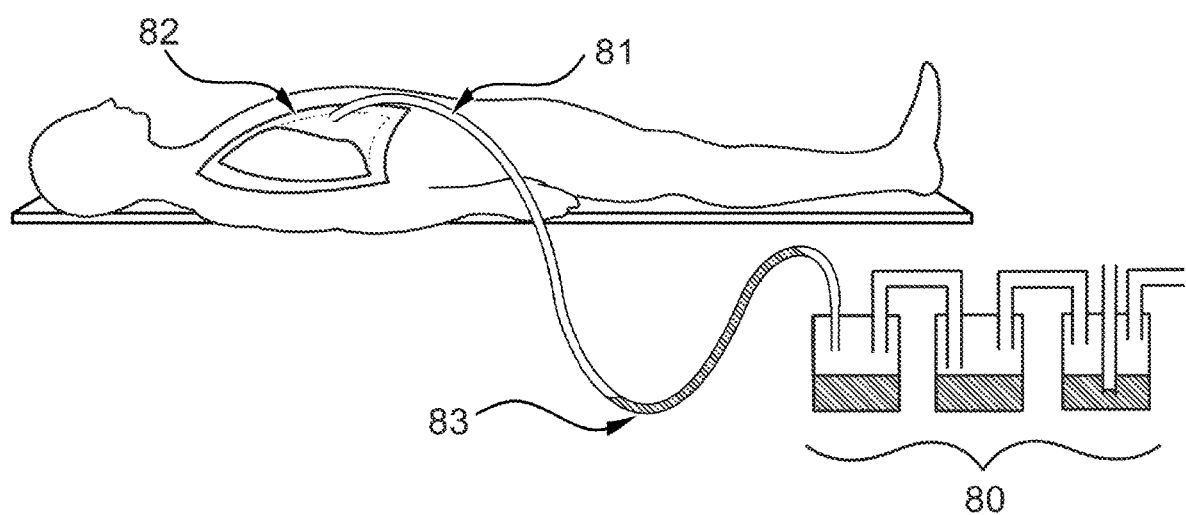
FIG. 8A shows a representation of a chest drainage system.
Figure 8B:
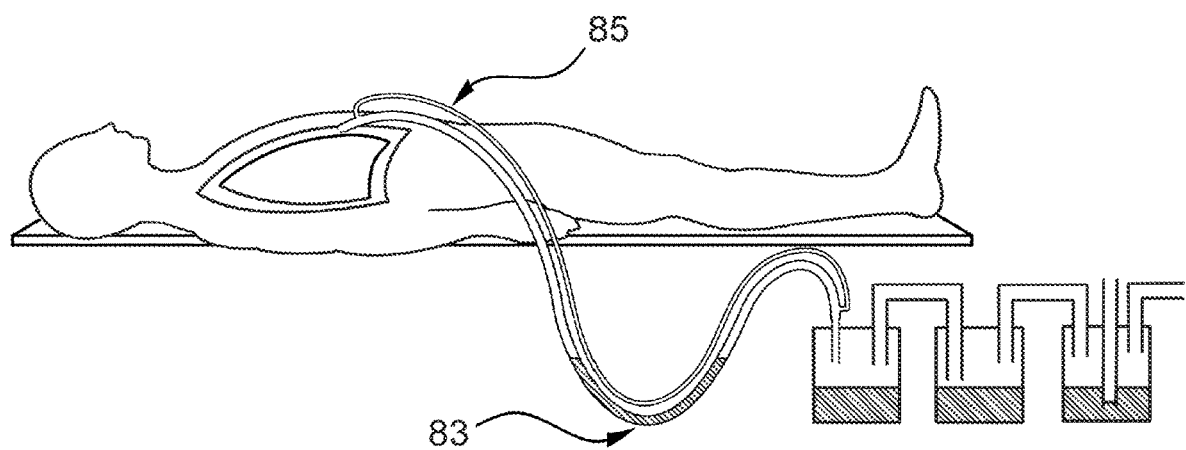
FIG. 8B shows a chest drainage system with an external bypass according to an embodiment of the invention.
Figure 8C:
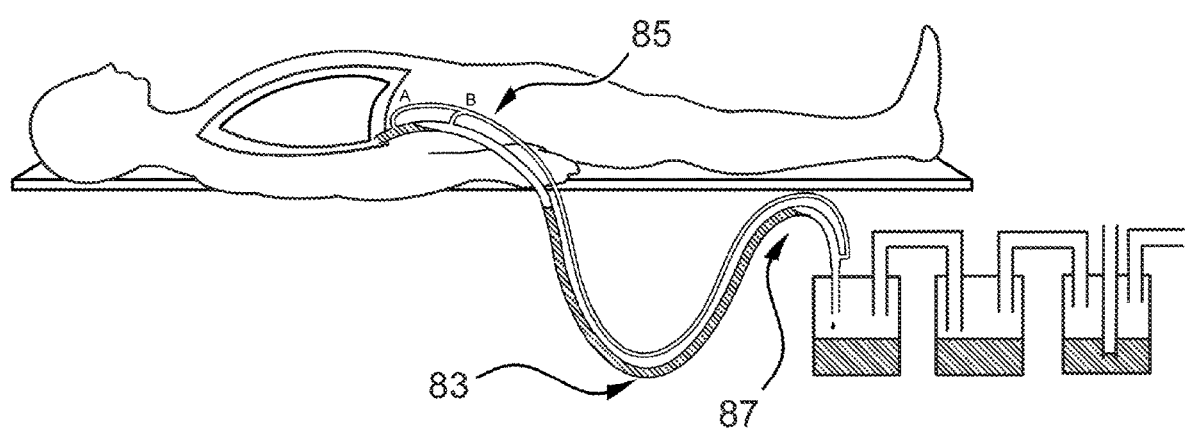
FIG. 8C shows a chest drainage system with an external bypass according to another embodiment of the invention.

In a chest tube application, as shown in FIGS. 8A-8C, a vacuum source would be applied via a chest drainage system 80 to a drainage tube 81, such as a thoracic drain tube, connected to a chest tube inserted in the pleural space 82 of a patient. The chest tube is intended to transmit and maintain a negative pressure (slight vacuum or sub-atmospheric pressure) in the pleural space in which it is inserted. In clinical practice, it is observed that the chest drainage tube will also form liquid-filled loops 83 and that just like in FIG. 1B, the downstream meniscus is higher than the upstream meniscus indicating that the pressure in the upstream air pocket is higher than the vacuum applied at the chest drainage system

80. This formation of liquid-filled loops in chest drainage assemblies leads to the manufacturers' recommendation that clinicians "milk" the chest drainage tube, i.e., empty the liquid-filled loop, similar to "milking" a urinary drainage tube. According to an embodiment of the invention such as shown in FIG. 8B, a venting port is provided at the upstream air pocket to connect the upstream air pocket to the vacuum at the chest drainage system via a bypass lumen 85 (that bypasses the liquid-filled loop) in order to help transmit the vacuum to the chest tube in spite of the water trap generated by the liquid-filled loop. A hydrophobic or other such liquid-repellent, but gas permeable membrane can be disposed at the venting port to inhibit a given liquid or liquids from entering the bypass line. The particular gas-permeable membrane can be selected based on the liquid needing to be repelled. For example one gas-permeable membrane may be suitable for water, another for blood, and yet another for urine. In a further embodiment such as shown in FIG. 8C, the venting port to bypass lumen 85 is provided in plurality.

In one embodiment, the patient-side drainage tubing/bypass channel connection is disposed higher than the distal apex 87 at the canister side (or drainage bag side for urinary drainage systems). In such a position, if fluid accumulates in the dependent loop 83 as in the example of FIG. 8C and is left undrained for long periods of time, the maximum height that the patient side meniscus reaches will be limited to the height of the distal apex 87. Further fluid collection after the canister side meniscus has reached the distal apex 87 results in liquid flowing into the drainage canister as in FIG. 8C. By placing at least one of the patient-side drainage tubing/bypass channel connections higher than the distal apex in the configurations in which a chest drainage system is clinically used, then the membrane of the at least one bypass channel connection may be able to avoid blockage from standing bodies of liquid.

Similar to the urine drainage systems, the catheter/drainage tubing combination in a chest drainage system may make a small convex curve as the catheter/drainage tubing leaves the patient as shown in FIG. 8C. If the location of a sole patient-side drainage tubing/bypass channel connection is on the ascending limb (such as venting port A in FIG. 8C) and the ascending limb is filled with liquid as shown in FIG. 8C, the bypass will not work. If the patient-side drainage tubing/bypass channel connection is on the descending limb (such as venting port B in FIG. 8C), the likelihood of the venting port being submerged or adjacent to a body of liquid is decreased because there is less probability of liquid accumulation in the descending limb at vent B. Therefore, the likelihood that the bypass will be able to work as intended is substantially increased if the connection is at the descending limb. Because the exact location of the descending limb cannot be determined a priori in chest, urine and other drainage systems, a multitude of vents and/or bypass connections increases the probability that one of the vents and/or connections will be at location free of liquid. A multitude of vents and connections also allows more than one air or gas pocket to be vented if there is more than one air or gas pocket. By providing multiple venting port locations as described with respect to certain embodiments, it is possible to improve the performance of the bypass line or venting lumen.

In-vitro experiments conducted in association with prototype embodiment tests have shown that, in drainage systems, there is also a vacuum or pressure loss or perturbation across the drainage catheter if there is fluid accumulation in the catheter (as distinct from the drainage tubing) or an ascending limb of the drainage tubing. The pressure or vacuum change in units of cm $H_2O$ at the catheter and/or drainage tubing is equal to the vertical elevation (in cm) of the column of liquid, when the liquid is water or has a density close to the density of water. For example, the fluid accumulation in the catheter and/or an ascending limb of the drainage tubing is shown in FIG. 8C as it relates to the chest drainage example. According to an embodiment, for the purpose of determining, estimating, compensating or adjusting the pressure or vacuum at the location or organ being drained, it can be helpful to measure the vertical elevation spanned by the two menisci of the body of liquid at vent A in FIG. 8C and factor that loss in the calculation, measurement or remedial action or to configure the drainage system so that liquid cannot accumulate in the catheter and/or the drainage tubing immediately adjacent to the catheter.

For certain of the embodiments having multiple venting port locations, the multitude of vents can be provided as multiple vents along the drainage tubing, as a drainage tubing with a strip of a gas-permeable membrane along its length, or as a drainage tubing with a smaller internal tube made of a gas-permeable membrane. In one embodiment, a venting channel separated from the interior of the drainage tubing by a gas permeable membrane or a conduit made of the gas permeable membrane can extend at least a third of the distance of the drainage tube, enabling gas/air to vent along the interior of the drainage tube. The length of the channel or conduit can be such that the channel or conduit does not extend to the ends of the drainage tubing or only extends to one end of the drainage tubing. These above described configurations can be used to ensure that a drainage system has a working vent to inhibit the formation of undesirable backpressure or suction during clinical use, irrespective of the configuration of the drainage system (see also FIGS. 14, 15A-15C, 16A, 16B and 17 and the description related thereto).

If the chest tube is inhibited from transmitting a vacuum by the liquid-filled loop, complications such as unnecessarily extended length of stay, low blood pressure, and emergency surgery may arise. For example, recent data suggests that, in cardiac surgery patients, chest tube use is associated with longer lengths of stay (average 23.7 days) compared to patients who did not have a chest tube (average 10.4 days).

One possible reason for this difference in lengths of stay may be attributed to residual pneumothorax. A residual pneumothorax is a pneumothorax (PTX) that persists after chest tube placement instead of being resolved by the chest tube drainage.

Current procedures involve taking a daily supine anteroposterior chest X-ray of a patient with a chest tube to assist in chest drainage tube management. The criterion for chest tube removal generally depends on the indication for the chest tube placement. If the patient needed the chest tube because of PTX, the chest x-ray will be evaluated each day for the presence or absence of the PTX. In addition, the chest drainage canister is checked for the presence of an air leak. To check the drainage canister for an air leak, the suction on the container is held and the patient is asked to cough (increasing intrapleural pressure). The existence of an air leak is signified by the presence of bubbles in the water chamber of the drainage canister and means that air is still escaping from the lunch parenchyma. In such a case, the chest tube cannot be removed. However, if the chest x-ray demonstrates no PTX and there is no air leak, then the tube will be removed and a follow up chest X-ray is performed to determine that no PTX was caused by removal of the tube.

The decrease of the applied suction by the undrained fluid in a dependent loop may predispose a patient to unresolved PTX. If the undrained dependent loop causes less suction, then the amount of vacuum set for the drainage system is not actually being applied to the intrapleural space. In addition, the current routine of performing daily supine anteroposterior chest X-rays may not be the best or most sensitive test for residual PTX.

However in another approach, if the indication for the chest tube was drainage of fluid, then the daily chest X-ray can be evaluated for the presence of fluid. The amount of daily drainage is assessed and, in general, if the chest tube output is less than 200 ml and the chest X-ray demonstrates little to no effusion, then the tube is pulled. However, if the chest tube output is greater than 200 ml, the tube is usually left in so as to avoid having to reinsert a tube due to re-accumulation of effusion. Here again, the reduction in transmitted vacuum from the undrained dependent loop may lead to reduced effusion that is not a sign of patient improvement, but a result of reduced suction, leading to decreased exudate being suctioned out of the lungs.

Because the average cost of a non-admission hospital day in the US is estimated at $3000/day, reducing the length of stay saves substantial costs. Therefore, certain embodiments of the invention can be applied to chest drainage systems in order to improve the appropriate vacuum being applied at the intrapleural space to remove fluid.

In further embodiments, the venting port/bypass lumen can also be used to equalize the pressure between an upstream air pocket and a downstream air pocket when the vacuum is no longer applied, as in the case where active drainage is no longer being performed prior to removing the chest tube. This may help reduce problems during removal of the chest drainage tube. Among other implementations, the bypass lumen can be implemented in the same way as the venting lumen for the urine drainage system, i.e., as an internal separate lumen, an external lumen that is separate or attached to or extruded with the drainage tube or extruded in the wall of the drainage tube.

In addition, certain embodiments of the invention can be implemented to address the difficulty in ascertaining the actual vacuum being delivered in a chest drainage (or other) system. For example, some current chest drainage canisters include a device to indicate the vacuum being delivered. However, this device is misleadingly labeled "Patient pressure." It is misleading because, due to the interference of undrained dependent loops with passive and active drainage systems, it is clear that the pressure measured at the canister does not reflect the pressure at the chest drainage catheter tip.

Accordingly, certain embodiments include a sensor for measuring pressure by sampling pressure at the catheter tip. As one approach, a small bore pressure sampling tube can be used to measure pressure at the catheter tip. However, in certain situations this tube gets clogged with fluid and may not measure the pressure reliably. Therefore, according to one embodiment, one or more inexpensive, disposable solid state pressure sensors can be provided at or near the tip of the catheter to relay the pressure reading back by wire or wirelessly. In certain embodiments, the pressure senor and the wire(s) are imbedded in the wall of the catheter. The pressure sensor can be a MEMS-based pressure sensor or other semiconductor or CMOS process-fabricated design.

According to an embodiment, a system is provided that can prevent the formation of loops where liquid can collect and ensure a monotonic downhill gradient or at least prevent uphill gradients on the way to a drainage receptacle. Such systems can ensure free, unimpeded flow of urine that may be especially important for newly transplanted kidneys. Of course, other applications are contemplated.

A monotonic downhill gradient is not necessarily a constant gradient. In a coordinate system where the horizontal is x and the vertical is y, a monotonic gradient can be defined as a gradient where the second derivative of y with respect to x ($d^2y/dx^2$) is never zero, i.e., there is no inflection point in the drainage tubing. The first derivative of x with respect to y (dy/dx) can be zero, i.e., portions of the gradient can be horizontal. With a monotonic downward gradient, no downstream part of the tubing will be higher in elevation than any upstream part of the tubing. As a result: (a) no urine-filled loops will be formed that throttle urine outflow and (b) no urine will collect in the tubing that can flow back to the bladder if the tubing is inadvertently placed above the bladder.

In accordance with one embodiment of the invention, in order to eliminate or substantially reduce formation of loops where liquid can collect or obstruct the tubing cross-section, the drainage tubing is configured so that there is a monotonic downward gradient from the bladder to the Foley bag.

In certain embodiments, the system can include mechanical templates that can be mounted on IV poles, OR beds, stretchers, gurneys, patient transport devices, wheelchairs, etc. that ensure that each downstream element of the drainage tubing is lower, or not higher, than the adjacent upstream component. In a specific embodiment, the mechanical template to shape a tube can be in the form of a groove for threading the drainage tube. For example, mechanical templates can be provided with spiral, zig-zag shapes, or grooves that make the drainage tubing conform to the requirement that no downstream element is higher in elevation than an upstream element.

Figure 9:
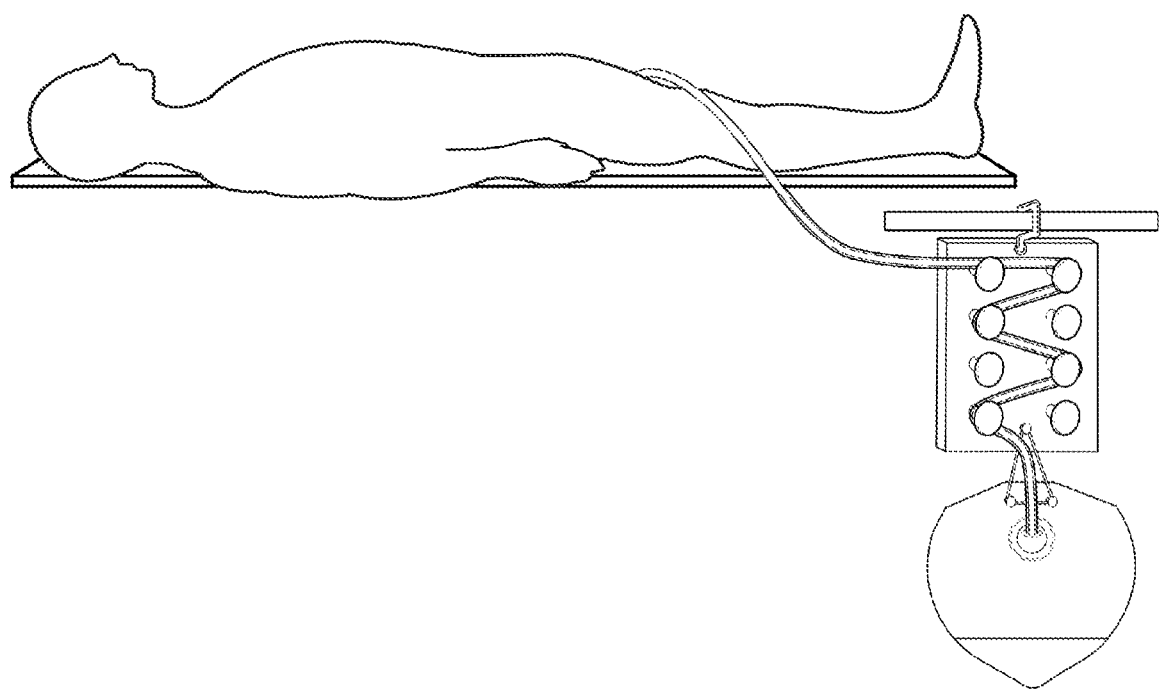
FIG. 9 shows a representation of a backflow optimization system with a mechanical template according to an embodiment of the invention.
Figure 10A:
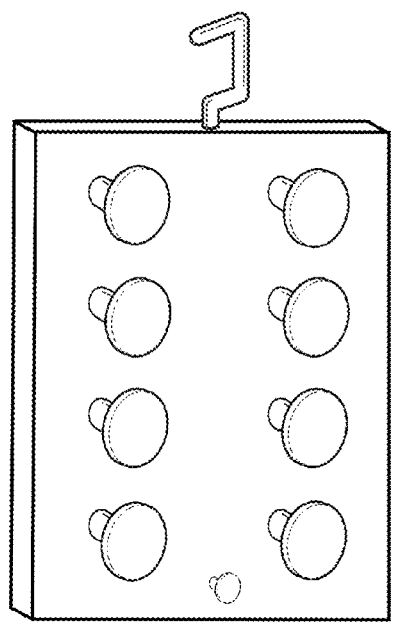
FIGS. 10A-10C show representations of mechanical templates to shape a drainage tube in accordance with certain embodiments of the invention.

Referring to FIGS. 9 and 10A-10C, backpressure can be alleviated by providing a monotonic downward gradient of the drainage tube flow. The monotonic downward gradient can be accomplished by threading the existing drainage tube of a Foley assembly on pegs provided at or near the hook for the Foley collection bag, such as shown in FIGS. 9 and 10A. The pegs can be straight or hooked. The pegs can also be provided extending out at an upward angle so that the drainage tube can catch on the peg and be inhibited from sliding out. Advantageously, the peg assembly provides a mechanism that only requires the caregiver to use one hand because no snaps or bands are required to keep the tube in place.

Figure 10B:
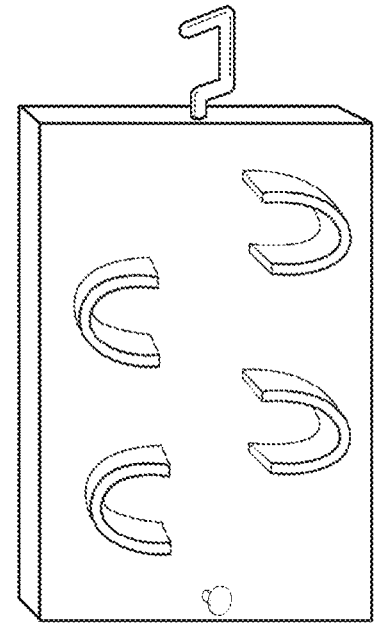
Figure 10C:
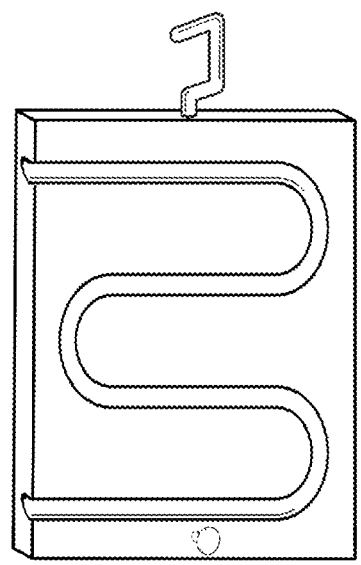

According to another embodiment, as shown in FIG. 10B, a bracket assembly can be provided to thread the drainage tube into the monotonic downward gradient. The bracket assembly can include a lip along the outer edge to keep the drainage tube from sliding out. In yet another embodiment, a groove assembly can be provided as shown in FIG. 10C into which the drainage tubing is snapped.

For embodiments also incorporating the subject context-sensitive flow interrupter, the holder portion can be provided at or near the mechanical template.

In a further embodiment, the mechanical template can include additional features such as holders for alcohol swipes, a slot for smart phones with inclinometers, and a built-in water level.

To the extent that the templates can inhibit accumulation of liquid in dependent loops, milking, which may result in suction being applied to the bladder, will likely not be performed. By avoiding creating a situation where milking could be used to alleviate the accumulation of liquid, the templates can also reduce the likelihood of suction being applied to the bladder.

Figure 12A:
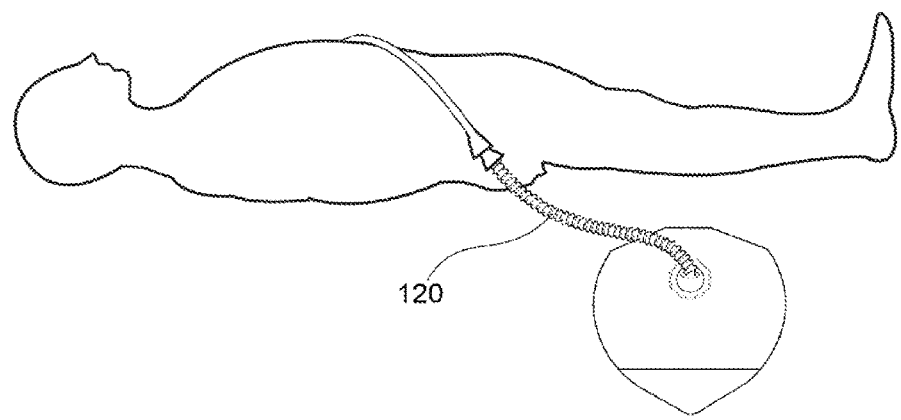
FIGS. 12A and 12B show representations of a system utilizing a corrugated hose in accordance with an embodiment of the invention.
Figure 12B:
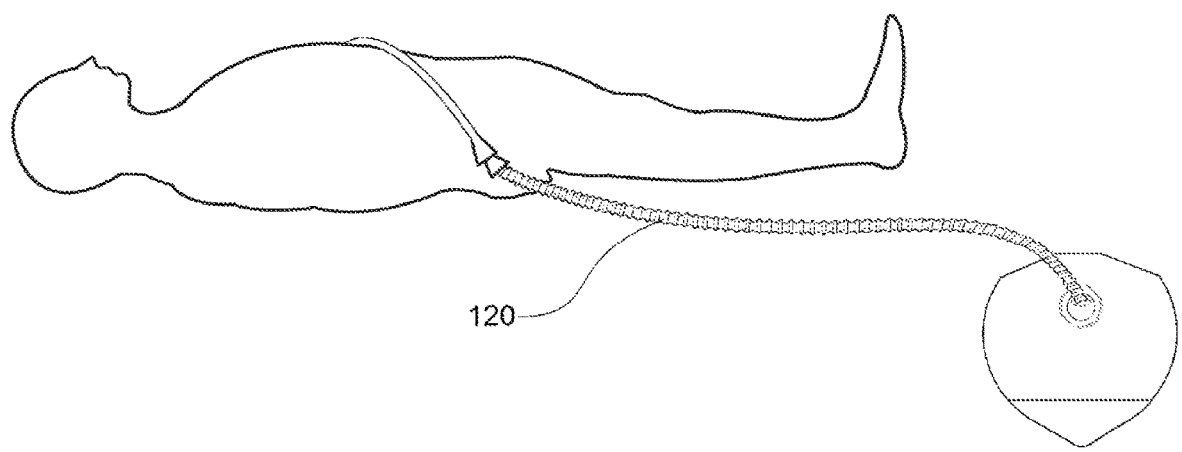

A corrugated hose 120, such as shown in FIGS. 12A and 12B, whose length can be increased or shortened by extending or compressing the corrugations respectively can also be used to take up any slack in the drainage tubing to prevent the formation of loops and provide a monotonic gradient. Some corrugated hoses may maintain their shape when the corrugations are compressed. The corrugations can trap a small amount of liquid at the trough of each corrugation. By making the corrugations as small as possible, the amount of liquid trapped may be minimized. If it turns out that the small amount of urine trapped leads to infection within x days, then this design may be recommended for situations where it is known a priori that the Foley will be in place for less than x days. This introduces the concept of drainage systems optimized for the expected duration of use instead of a "one size fits all" drainage system.

A malleable (shape memory) drainage hose that retains its configuration and can be shaped to provide and retain a monotonic gradient is also contemplated. The hose may be made malleable through the material used to manufacture it or a malleable insert could be embedded, extruded or attached with the drainage tube along part or all of its length.

Foley drainage tubing is currently thick-walled, presumably to prevent kinking (that would create flow obstruction) when loops are present. By preventing the formation of loops where liquid can collect, it is possible that the Foley tubing (or other drainage tubing) wall may be allowed to be made thinner because without loops, there is a less chance of kinking. For example, if there is no slack in the drainage tube because the drainage tube is tidily shaped by a mechanical template, there is less chance of kinking. The thinner tubing walls can result in lower material costs. In addition, thinner walls may make it easier to conform the tubing to the pre-shaped grooves of certain embodiments of the invention. The drainage tubing does not necessarily need to be of uniform wall thickness along its length, as is currently the case, and could be of variable wall thickness along selected portions of its length.

According to another embodiment, backpressure and/or suction is alleviated by a venting system in the drainage tube. In such embodiments, there is no need to prevent loop formation because the venting system controls the backpressure and/or suction experienced by the bladder (or other organ, space, or cavity).

The venting system can provide a pressure adjustment along one or more locations within the drainage tube or Foley or drainage assembly. The particular locations can be based on where loops tend to form and/or at or near the Foley catheter or at the bladder itself. The venting system can include a venting tube internal or external to the drainage tube or extruded within a wall of the drainage tube. In one embodiment, multiple vent tubes or lumens can be extruded within the wall of the drainage tube. The multiple vent tubes can be exposed to the interior of the drainage tube at one or more locations along the tube or Foley assembly. The exposed openings can be protected with a gas-permeable membranes that is hydrophobic or that can block urine or liquid or blood from flowing into the venting tube. An example of a hydrophobic gas-permeable membrane is PTFE membrane with 0.2 micron pores such as that used in the Millipore syringe filter (SLFG025NS).

Figure 11:
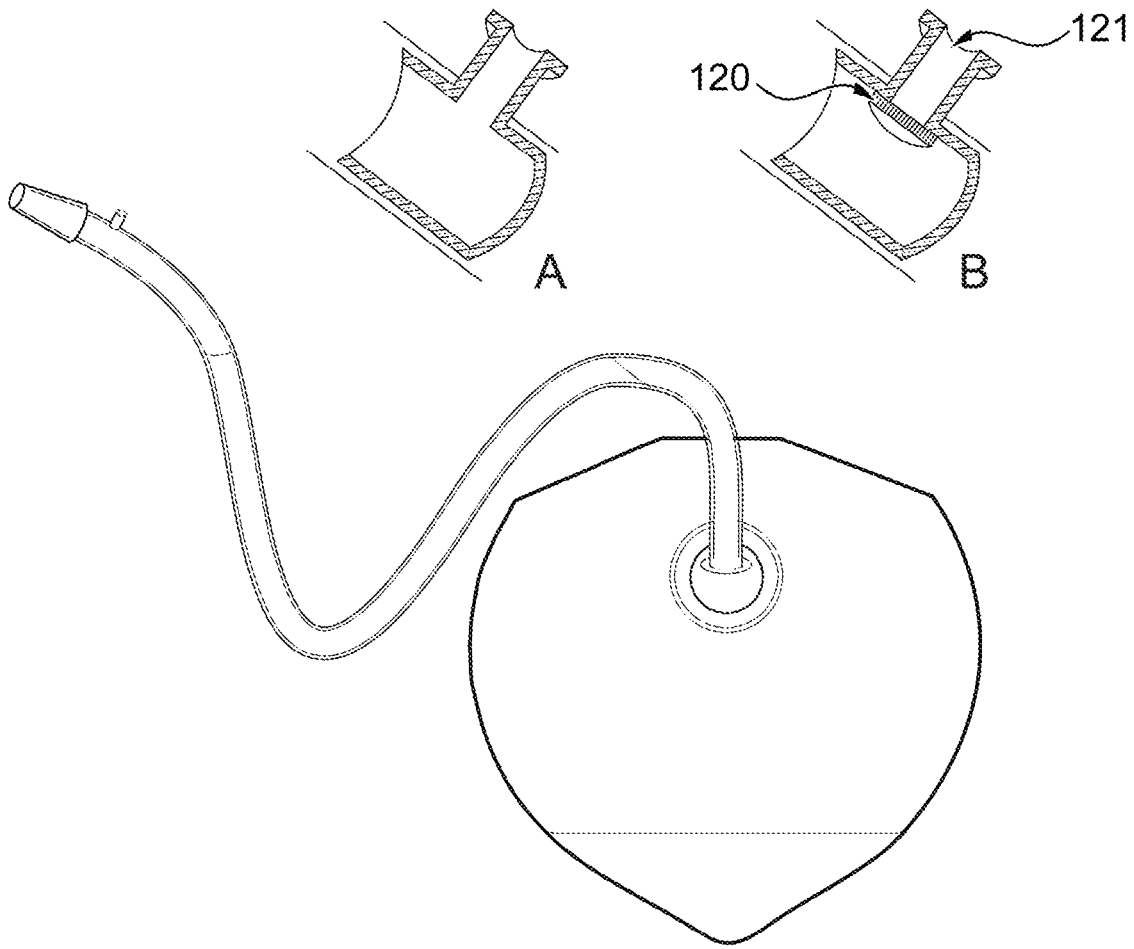
FIG. 11 shows representations of a backflow optimization system with vent with (B) and without (A) gas-permeable membrane according to an embodiment of the invention.

Referring to FIG. 11, venting the airspace U to the atmosphere changes the pressure and results in an equalization or an adjustment of pressure between the airspace U and the airspace D (as illustrated by the menisci of the fluid at the loop being about equal in height). This allows for improved urine flow into the collection bag and better bladder emp-tying because there is minimal backpressure (or unwanted suction) on the bladder and the operating point of the bladder has been moved from approximately coordinate B (425, 20) to approximately coordinate A (20,0) in FIG. 2.

In order to accomplish this adjustment, in one embodiment as shown in FIG. 11B, the airspace U in the drainage tube can be directly vented to atmosphere using a gas-permeable patch 120, for example, one similar to that used on the Foley bag or the Millipore material. The port 121 connected to the vent can be for example a slip fit port or Luer lock that accepts tubing that is used to connect the vent port to atmosphere, supra-atmospheric pressure or sub-atmospheric pressure (as in the case of a chest drainage system).

According to another embodiment of the venting port, a needle decompression kit can be provided that includes a sterile needle and a disinfectant for disinfecting the external surface of a drainage assembly where it will be punctured. This provides a quick way to decompress a compressed air pocket and vent it to atmosphere, sub-atmospheric pressure or supra-atmospheric pressure. In such an embodiment, a user can disinfect the external surface first and then stab the needle through the tubing wall (that may be made of a self-sealing material) into the air pocket, allowing the pressure to equilibrate to atmosphere. Like the vent port, the needle can have a slip fit or Luer lock to connect to tubing that connects the vented space to the desired pressure.

Figure 13A:
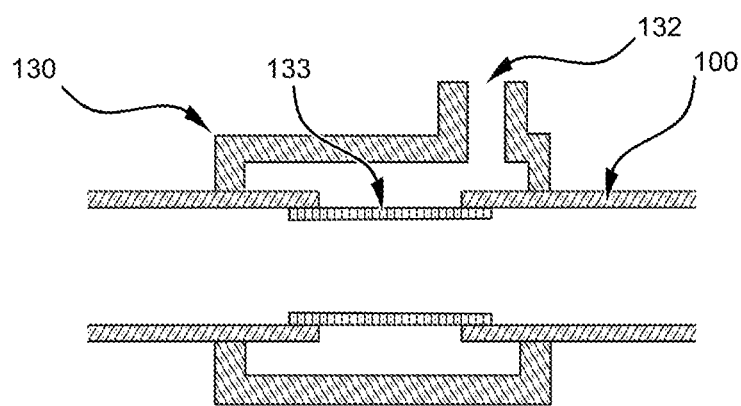
FIGS. 13A and 13B show representations of a venting system with a venting collar according to an embodiment of the invention.
Figure 13B:
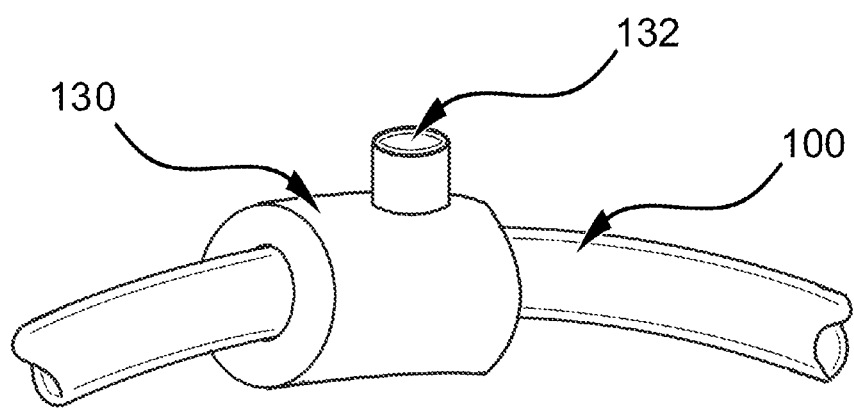

As shown in FIGS. 13A and 13B, a venting collar 130 can be used to vent a drainage tube 100 to atmosphere, supra-atmospheric or sub-atmospheric pressure. The venting collar 130 can be of different shapes (cylinder, sphere, rectangular, etc.). An opening 132 in the venting collar 130 can be used to vent the drainage tube 100 to the atmosphere, the desired pressure or to another chamber. The wrap-around or circumferential layout of the vent port 133 (covered with a gas-permeable membrane), ensures that the vent port 133 will vent irrespective of the location of an air pocket if the drainage tube 100 is only partially filled with liquid. By having a wrap-around layout of an gas permeable membrane, problems with venting such as in a case where a cross-section of drainage tubing has both liquid and gas and the vent port was at only one location, which happens to be submerged (thereby inhibiting venting), can be avoided.

In another embodiment, the airspace U can be in pneumatic connection to the inside of a vented collection receptacle. This can be accomplished using, for example, an external tube, an internal tube, or an inbuilt venting lumen embedded in the wall of the drainage tube.

In one embodiment, as shown in FIG. 14, an internal tube 141 can run a portion of the length of the drainage tube 100. In another embodiment, as shown in FIGS. 15A-15C, an inbuilt venting lumen can be embedded (or extruded) in the wall of the drainage tube and include an opening on the interior surface of the drainage tube at the venting port locations. In FIG. 15C, the cross-section is made at the venting port 152 that connects to the interior of the drainage tube. The cross-section of the inbuilt venting lumen 150 in FIG. 15C can be of any appropriate shape or size. The oval shape is shown as one possible cross-section that would facilitate closing/crushing of the venting lumen when used with a context-sensitive flow interrupter such as a clamp.

For the embodiments shown in FIGS. 14 and 15A-15C, the opening of the venting tube to the airspace in the drainage tube can include a membrane (see membrane 142 of FIG. 14) that blocks liquid from flowing into the venting tube.

Figure 17:
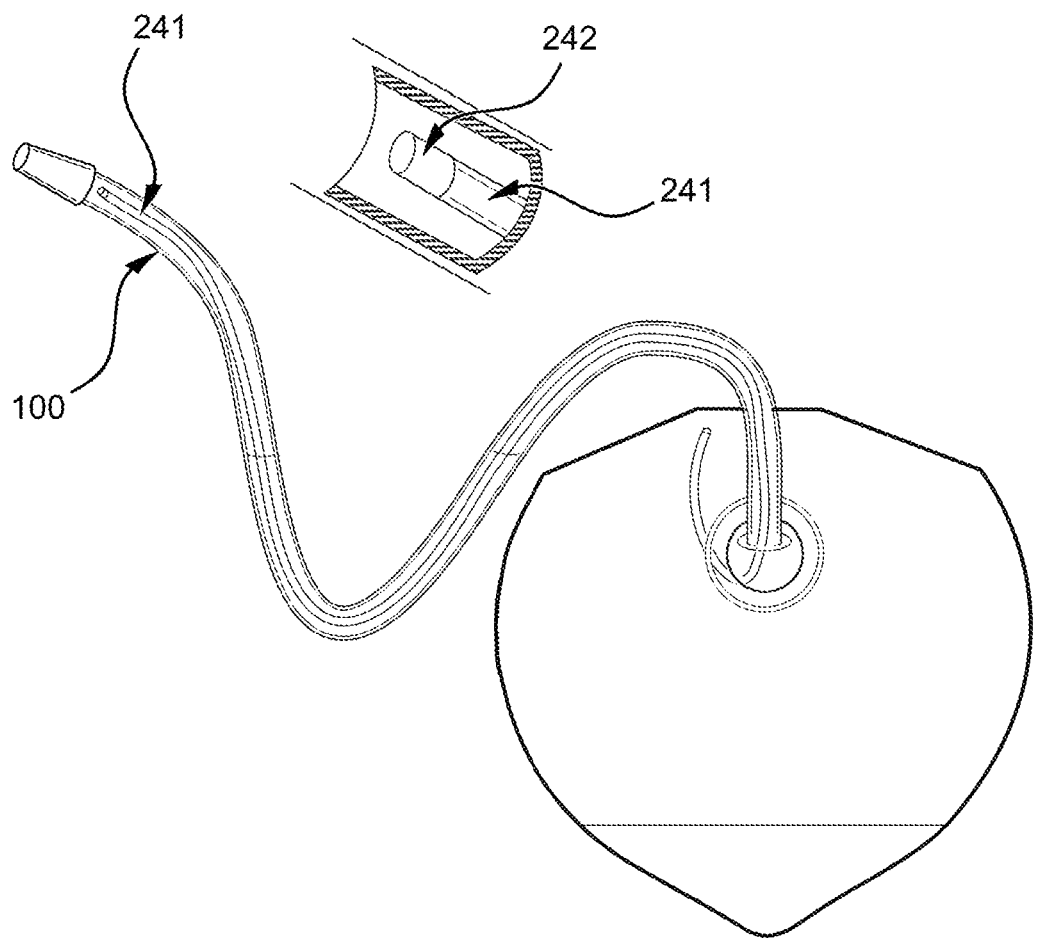
FIG. 17 shows a representation of a venting/bypass system with internal venting/bypass tube according to an embodiment of the invention.

In an embodiment, as shown in FIG. 17, instead of a membrane 142 at an opening of the venting tube 141 (as shown in FIG. 14), an internal tube 241 can be provided having walls formed entirely, substantially, or mostly of a gas permeable membrane material. This internal vent tube 241 can run at least a portion of the length of the drainage tube 100. A plug 242 can be provided at an end of the vent tube 241 to inhibit liquid from entering the vent tube 241.

A drainage tube with the addition of a vent in accordance with an embodiment of the invention does not need to be manipulated or milked to relieve backpressure (or suction); in addition, tests of an embodiment of the subject vent indicate that no negative pressure or siphon developed.

In a further embodiment, a controlled back-pressure is applied to the subject venting system to inhibit bladder collapse due to a potential siphon effect or to inhibit back flow during milking (emptying a drainage tube of accumulated liquid). In particular, the Foley catheter may act as a siphon if its connection to the drainage tube is lower than its entrance to the bladder, as is the case when a patient is laying flat and if the external portion of the Foley catheter is routed below the patient's thigh. This siphon action can pull a slight negative pressure on the bladder at the end of bladder emptying. Accordingly, certain embodiments of the invention provide a small amount of backpressure in the drainage tube to balance the siphon effect of the Foley catheter. According to an embodiment of the invention, the venting tube includes a shunt having gas-permeable membranes at both ends. Placing the distal end of the shunt at a position below a few cm of urine or other fluid, either in a special chamber inside or outside the collection receptacle or by terminating it in the downstream leg of the loop will cause the pressure in the upstream leg to be a corresponding number of cm of urine higher than atmospheric pressure. The backpressure can then be adjusted using, for example, a lever or spring that adjusts the relative depth of immersion of the distal end of the shunt with respect to the surface of the liquid it is placed in. Making this additional pressure head adjustable inhibits both over-pressurization and suction of the bladder.

In open channel flow as compared to closed channel flow, pressurized gas pockets cannot form because an open channel has continuous access to atmosphere and is thus continuously "vented". However open channel flow can be messy, for instance, if the liquid overflows the open channel and spills outside. On the other hand, a closed channel like a closed tube contains the liquid and prevents it from spilling and causing a mess but is subject to the formation of gas pockets or airlocks that can then create back pressure and impede flow.

Accordingly, in one embodiment of the invention, a general purpose tube with a quasi-continuous slit 160 running along its length is provided. The slit is quasi-continuous, instead of continuous as can be provided in other embodiments, because there are connecting pieces of the tubing material at intervals to maintain the mechanical integrity and cross-section of the tube as for example in FIG. 16. Such a tube with a quasi-slit running throughout its length would behave like an open-channel. If a continuous or non-continuous strip of a gas-permeable membrane is attached to the entire length of the quasi-slit along the internal and/or external surface, then the tubing is converted into a closed channel that constrains the liquid flowing through it but is continuously vented along its length.

Figure 16A:
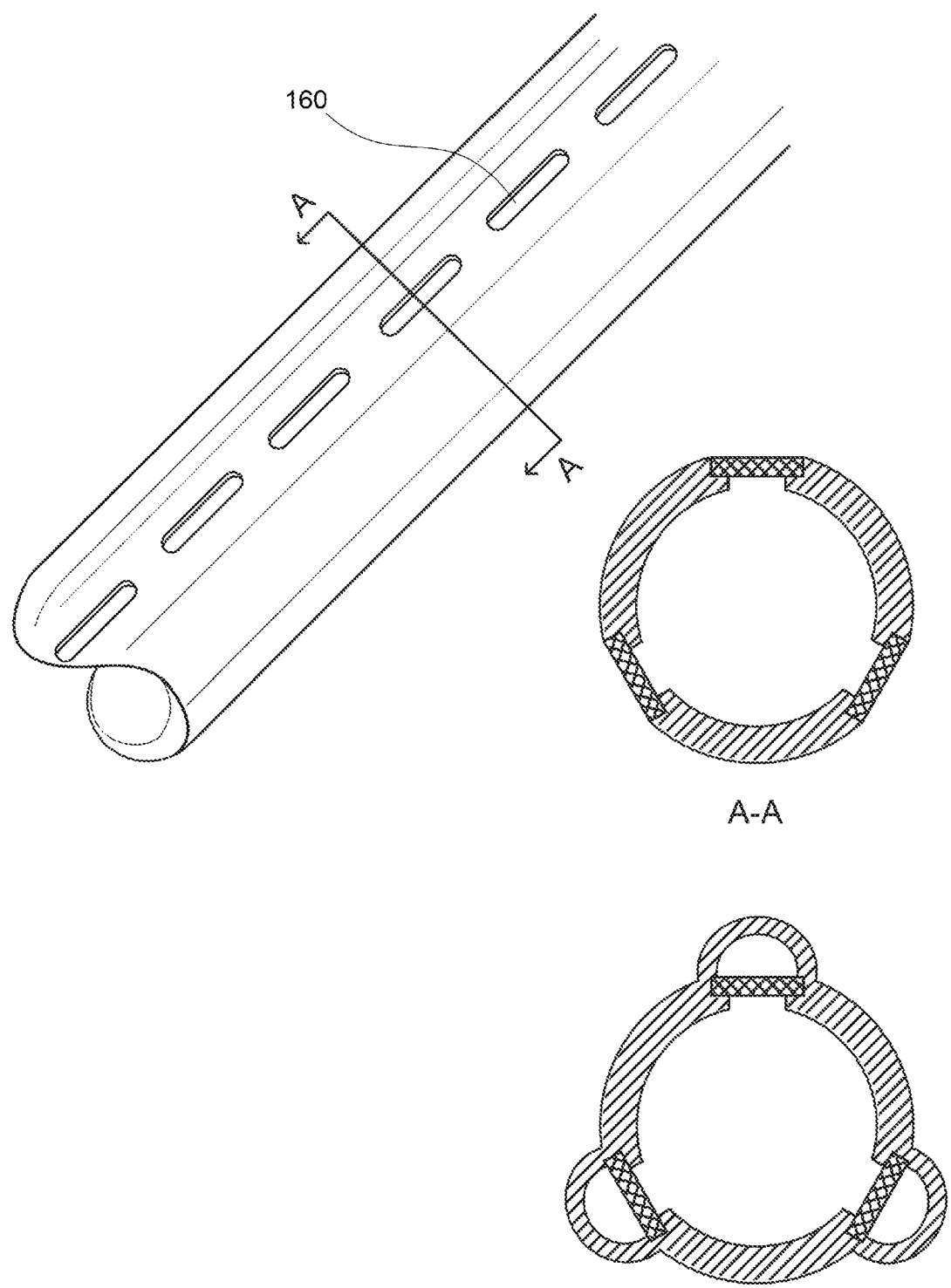
FIG. 16A shows a representation of a general purpose tubing with a quasi-continuous venting strip according to an embodiment of the invention.
Figure 16B:
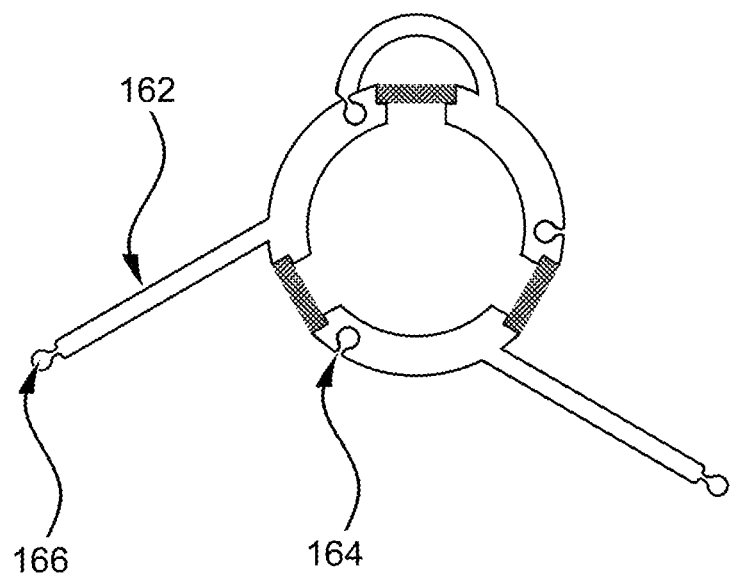
FIG. 16B shows a representation of snap-on lumens for a quasi-continuous venting strip according to an embodiment of the invention.

The cross-section A-A in FIG. 16 shows three strips of a gas-permeable membrane running along the length of the tube with the cross section performed at a location where there are slits. As an alternative embodiment, the strips can form enclosed lumens as shown in the alternate cross-section, especially if the tube is not vented to atmosphere but to some other desired pressure. The tube would be extruded as for section A-A except that, running next to the slit, there would be a continuous flange 162 whose free end is then bent over after extrusion and bonded back to the tube to create a lumen. In the embodiment shown in FIG. 16B, there is a corresponding slot 164 that runs along the quasi-slit. To create the lumen, the tip 166 of the flange is bent over and inserted into the slot 164 forming a lumen. The connection between slot 164 and tip 166 can be made airtight by glue or ultrasonic welding. Thus, the tube would offer the benefits of both closed channel flow (containing the liquid flowing through it) and open-channel flow (no formation of air locks). For other applications where the liquid is not water or the gas is not air, the membrane would be selected to vent the desired gas but prevent passage of the liquid that needs to be kept out.

Accordingly, embodiments are provided that can control outflow and back-flow in drainage systems. In certain embodiments, existing drainage systems can be retrofitted or directly applied with features implementing the subject context-sensitive flow interrupter and/or outflow optimization system.

In accordance with embodiments of the invention, methods of venting a drainage tube, methods of providing context-specific flow interruption, fluid outflow optimization apparatuses, fluid back-flow prevention apparatuses, integrated systems to control outflow and back-flow, kits for draining a biological fluid from a site in a subject, and kits for modifying an existing conventional Foley assembly are provided.

The terms bag, canister, and receptacle have been used interchangeably in certain embodiments of drainage systems described herein. It should be understood that the described receptacles can be in the form of canisters, chambers, bags, and other structures depending on the particular drainage system application. For example, in urinary drainage systems, the receptacle is usually a Foley bag; and in chest drainage systems, the receptacle is usually in the form of a canister or a structure having a collection chamber.

It should be understood that embodiments described with respect to a urinary drainage system can be applied to other drainage systems and embodiments described with respect to a chest drainage system can be applied to other drainage systems, and these examples should not be construed as limiting a particular drainage configuration to those explicitly described applications.

Embodiments of the invention include, but are not limited to:

1. An apparatus for inhibiting fluid flow along a drainage path between a drainage collection container and a source of the fluid, the apparatus comprising: an actuator portion on a section of a drainage path comprising a flow interrupter that inhibits fluid from passing through the drainage path at the section having the actuator portion; a holder portion that engages the actuator portion wherein interacting the actuator portion with the holder portion of the device changes the state of the flow interrupter of the actuator portion.

2. The apparatus according to embodiment 1, wherein the flow interrupter comprises a clamp, stopcock, or cuff.

3. The apparatus according to embodiment 1, wherein the flow interrupter comprises a normally closed clamp capable of bringing a first portion of an interior wall of a drainage tube in contact with a second portion of the interior wall of the drainage tube such that fluid is inhibited from passing through the flexible drainage tube, wherein interacting the normally closed clamp with the holder portion causes the normally closed clamp to open.

4. The apparatus according to embodiment 3, wherein the normally closed clamp comprises a jaw-opening spring clamp having two arms extending from the spring clamp and the holder portion can comprise one or more brackets or rods defining a receptacle for the jaw-opening spring clamp, the receptacle having a diameter or opposing sidewall spacing smaller than a distance between the distal ends of the two arms, wherein insertion of the jaw-opening spring clamp into the receptacle causes the distance between the distal ends of the two arms to decrease, thereby opening the jaw-opening spring clamp.

5. The apparatus according to embodiment 3, wherein the normally closed clamp comprises a resilient deformable material on or within the section of the drainage tube, wherein the resilient deformable material causes the section of the flexible drainage tube to be in a collapsed position until interacted with the holder portion.

6. The apparatus according to embodiment 1, wherein the holder portion is configured to support a drainage collection receptacle.

7. An apparatus for optimizing outflow in drainage assemblies, the apparatus comprising: a mechanical template to shape a tube, the mechanical template providing a monotonic downward gradient from a body cavity or space to a drainage collection receptacle for a drainage tube shaped with the mechanical template.

8. The apparatus according to embodiment 7, wherein the mechanical template comprises a peg, groove, or bracket assembly.

9. The apparatus according to embodiment 7, further comprising a drainage collection bag holder affixed at one end of the mechanical template for hooking the drainage collection receptacle thereto.

10. A drainage assembly comprising: a drainage tube having a pressure equalizing vent, and a drainage collection bag connected to the drainage tube.

11. The drainage assembly according to embodiment 10, wherein the pressure equalizing vent comprises an aperture in the drainage tube and a gas-permeable membrane for venting the drainage tube to atmosphere or a particular vacuum level while blocking liquid from passing through the aperture.

12. The drainage assembly according to embodiment 11, further comprising a collar around a section of the drainage tube having the aperture. The aperture and gas-permeable membrane can continuously or quasi-continuously wrap-around an entire circumference of a portion of the drainage tube.

13. The drainage assembly according to embodiment 11, further comprising an external tube extending from the aperture along the drainage tube to an equalizing receptacle that is vented to atmosphere or has an applied vacuum. The equalizing receptacle can comprise a fluid therein and the external tube is controllably immersed in the fluid in the equalizing receptacle to provide a desired back-pressure.

14. The drainage assembly according to embodiment 10, wherein the equalizing vent comprises at least one inbuilt venting lumen embedded in a wall of the drainage tube, wherein one end of the venting lumen is exposed to an interior of the drainage tube and the other end of the venting lumen is configured to be exposed to an interior of a drainage collection bag connected to the drainage tube, wherein the drainage collection bag is vented to atmosphere. The other end of the venting lumen may comprise an immersion portion for controllable immersion into a liquid in the drainage collection bag.

15. A drainage assembly comprising: a drainage tube having one or more pressure vents along a portion or all of the drainage tube length, whereby at least one vent will not be occluded by an adjacent body of liquid during clinical use, irrespective of the orientation or configuration of the drainage system. The drainage tube can be part of, for example, a urinary or chest drainage assembly.

16. The drainage assembly according to embodiment 15, wherein the one or more pressure vents each comprise an aperture in the drainage tube and a gas-permeable membrane for venting the drainage tube to a desired pressure, such as atmospheric pressure or a particular vacuum level, while blocking liquid from passing through the aperture.

17. The drainage assembly according to embodiment 16, further comprising a collar around a section of the drainage tube having the aperture. The aperture and gas-permeable membrane can quasi-continuously wrap-around a circumference of a portion of the drainage tube.

18. The drainage assembly according to embodiment 16, further comprising a venting tube or lumen extending from at least one aperture of the one or more pressure vents along the drainage tube to atmosphere or to a receptacle that is vented to atmosphere or under applied vacuum.

19. The drainage assembly according to embodiment 18, wherein the receptacle can be a drainage receptacle of the drainage assembly or a separate compartment.

20. The drainage assembly according to embodiment 15, wherein the one or more vents comprise at least one inbuilt venting lumen embedded in a wall of the drainage tube, wherein one end of the venting lumen is exposed to an interior of the drainage tube and the other end of the venting lumen is configured to be exposed to an interior of a drainage collection receptacle connected to the drainage tube. The drainage collection receptacle can be vented to atmosphere or under an applied vacuum.

21. A method of optimizing outflow in a drainage assembly, the method comprising providing a vent in a drainage path of the drainage assembly.

22. The method according to embodiment 21, further comprising providing a context-sensitive flow interrupter at one end of a drainage tube of the drainage assembly at or near a drainage collection bag of the drainage assembly for inhibiting back-flow of fluid from the drainage collection bag.

23. A method of controlling fluid flow in a drainage assembly, the method comprising providing a context-sensitive flow interrupter at one end of a drainage tube of the drainage assembly at or near a drainage collection bag of the drainage assembly for inhibiting back-flow of fluid from the drainage collection bag.

24. A drainage assembly kit comprising: a catheter; a drainage collection bag; and a drainage tube comprising a vent. The catheter can also include a vent. In addition, a sterile venting needle can be included in the kit.

25. The kit according to embodiment 24, wherein the vent comprises an inbuilt venting lumen embedded in a wall of the drainage tube, wherein the drainage collection bag comprises a venting receptacle for receiving an immersion portion of the venting lumen.

26. A drainage assembly kit comprising: a context-sensitive flow interrupter comprising: a drainage tube portion for affixing to a drainage tube, wherein the drainage tube portion comprises a clamp or stopcock; and a holder portion.

27. A drainage assembly kit comprising a catheter; a drainage collection bag; a drainage tube comprising a drainage tube portion of a context-sensitive flow interrupter; and a holder portion of the context-sensitive flow interrupter.

28. A drainage assembly kit comprising a catheter; a drainage collection bag; a drainage tube; and a mechanical template to shape a tube.

29. A method of controlling pressure and fluid drainage in a drainage system assembly, the method comprising: venting at least one location in the drainage system assembly to atmospheric pressure, sub-ambient, or supra-atmospheric pressure.

30. A method of controlling pressure and fluid drainage in a drainage assembly, the method comprising: venting to atmospheric pressure, sub-ambient, or supra-atmospheric pressure at least one upstream air pocket in a drainage assembly with a fluid filled loop.

31. A method of controlling pressure and fluid drainage in a drainage system assembly, the method comprising: obtaining a monotonic gradient in a drainage tubing.

32. A method of controlling fluid flow, the method comprising: automatically opening or closing a flow path interrupter when the flow path interrupter is engaged in a holder.

The above listed embodiments are merely provided as a sampling of embodiments of the invention and should not be construed as limiting the invention to the embodiments listed. In addition, the above numerated embodiments should not be interpreted as presenting key or essential features of the claimed invention that would otherwise limit the scope of the claims.

All patents, patent applications, provisional applications, and publications referred to or cited herein are incorporated by reference in their entirety, including all figures and tables, to the extent they are not inconsistent with the explicit teachings of this specification.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

What is claimed is:

1. A drainage assembly comprising:
a draining catheter;
a drainage tube comprising a first end connected to the draining catheter; and
a venting system comprising (a) a venting tube in fluid communication with the drainage tube, (b) a vacuum source in fluid communication with the drainage tube and configured to pull a vacuum on the drainage tube, and (c) a venting valve comprising a first end exposed to an inside of the drainage tube and configured to, responsive to a predetermined vacuum level in the draining tube being reached, cause gas to pass therethrough and into the drainage tube.

2. The drainage assembly according to claim 1, wherein the venting valve is a passive valve, configured to allow or restrict flow of liquid or gas when a predetermined pressure threshold value is reached, independent of an external force or an external mechanism.

3. The drainage assembly according to claim 1, wherein the venting system is configured to vent to atmosphere.

4. The drainage assembly according to claim 1, wherein the venting tube runs along a length of the drainage tube.

5. The drainage assembly according to claim 1, wherein the venting system is configured to limit suction at the first end of the drainage tube.

6. The drainage assembly according to claim 1, wherein the venting system further comprises a gas-permeable membrane for venting the drainage tube to a desired vacuum, while blocking liquid from passing through the membrane.

7. The drainage assembly according to claim 1, wherein the drainage tube further comprises a second end connected to a receptacle container.

8. The drainage assembly according to claim 7, wherein the venting tube is connected to the inside of the receptacle container.

9. The drainage assembly according to claim 1, wherein the venting tube is a lumen that is external to the drainage tube.

10. The drainage assembly according to claim 1, wherein the venting tube is connected to the drainage tube at the venting valve and is detached from the drainage tube elsewhere.

11. The drainage assembly according to claim 1, wherein the venting tube is connected to the drainage tube along a length of the drainage tube.

12. The drainage assembly according to claim 1, wherein the venting tube is extruded with the drainage tube.

13. The drainage assembly according to claim 1, wherein the draining catheter comprises:
a proximal end connected to the first end of the drainage tube; and
a distal end comprising a sensor for measuring pressure.

14. The drainage assembly according to claim 13, wherein the sensor comprises a pressure sampling tube for measuring pressure.

15. The drainage assembly according to claim 1, wherein the vacuum source pulls the vacuum on a time interval.

* * * * *